(12) United States Patent
Hayeri et al.

(10) Patent No.: US 12,220,263 B2
(45) Date of Patent: Feb. 11, 2025

(54) PHYSIOLOGICAL PROPERTY FORECASTING

(71) Applicant: BIO-CONSCIOUS TECHNOLOGIES INC., Vancouver (CA)

(72) Inventors: Amir Hossein Hayeri, Vancouver (CA); Ricardo Cacho, Vancouver (CA); Suvan Ashok Ramchandani, Vancouver (CA); Nicolas Brandt, Vancouver (CA); Aleksey Sher, Vancouver (CA)

(73) Assignee: BIO-CONSCIOUS TECHNOLOGIES INC., Vancouver (CA)

( * ) Notice: Subject to any disclaimer, the term of this patent is extended or adjusted under 35 U.S.C. 154(b) by 759 days.

(21) Appl. No.: 16/650,581

(22) PCT Filed: Sep. 26, 2018

(86) PCT No.: PCT/CA2018/051213
§ 371 (c)(1),
(2) Date: Mar. 25, 2020

(87) PCT Pub. No.: WO2019/060991
PCT Pub. Date: Apr. 4, 2019

(65) Prior Publication Data
US 2020/0229772 A1    Jul. 23, 2020

Related U.S. Application Data

(60) Provisional application No. 62/614,047, filed on Jan. 5, 2018, provisional application No. 62/563,078, filed on Sep. 26, 2017.

(51) Int. Cl.
*A61B 5/00*     (2006.01)
*A61B 5/024*    (2006.01)
(Continued)

(52) U.S. Cl.
CPC ............ *A61B 5/7275* (2013.01); *A61B 5/024* (2013.01); *A61B 5/14532* (2013.01);
(Continued)

(58) Field of Classification Search
CPC ...... A61B 5/7275; G16H 50/67; G16H 50/30; G16H 50/70; G16H 50/20; G16H 50/63
See application file for complete search history.

(56) References Cited

U.S. PATENT DOCUMENTS

| 5,971,922 A | 10/1999 | Seizaburou et al. |
| 6,923,763 B1 | 8/2005 | Kovatchev et al. |

(Continued)

FOREIGN PATENT DOCUMENTS

| WO | 2002100266 A1 | 12/2002 |
| WO | 2012123765 A1 | 9/2012 |

OTHER PUBLICATIONS

Andreassen et al., "A probabilistic approach to glucose prediction and insulin dose adjustment: description of metabolic model and pilot evaluation study", Computer Methods Programs in Biomedicine, vol. 41, issues 3-4, Jan. 1994, pp. 153-165.

(Continued)

*Primary Examiner* — Mallika D Fairchild
(74) *Attorney, Agent, or Firm* — Christensen O'Connor Johnson Kindness PLLC

(57) ABSTRACT

A computer-implemented method of facilitating physiological property forecasting for detecting disease complications is disclosed. The method involves receiving signals representing sensed physiological property indicators, each of the sensed physiological property indicators representing a sensed physiological property of a patient at a respective time and receiving signals representing one or more contextual indicators associated with the sensed physiological property indicators. The method also involves applying at (Continued)

least one classification criterion to the one or more contextual indicators to determine a patient state of a plurality of possible patient states, each patient state associated with a respective set of forecasting parameters and applying the set of forecasting parameters associated with the determined patient state to the sensed physiological property indicators to determine at least one forecast physiological property indicator representing a forecast physiological property of the patient at a future time. Other methods, systems and computer-readable media are also disclosed.

10 Claims, 24 Drawing Sheets

(51) Int. Cl.
  *A61B 5/145* (2006.01)
  *G16H 40/63* (2018.01)
  *G16H 40/67* (2018.01)
  *G16H 50/20* (2018.01)
  *G16H 50/30* (2018.01)
  *G16H 50/70* (2018.01)
(52) U.S. Cl.
  CPC ............ *G16H 40/63* (2018.01); *G16H 40/67* (2018.01); *G16H 50/20* (2018.01); *G16H 50/30* (2018.01); *G16H 50/70* (2018.01)

(56) References Cited

U.S. PATENT DOCUMENTS

| | | |
|---|---|---|
| 2007/0078314 A1 | 4/2007 | Grounsell et al. |
| 2011/0184267 A1 | 7/2011 | Duke et al. |
| 2014/0066890 A1 | 3/2014 | Sloan et al. |
| 2014/0309511 A1* | 10/2014 | Stal .................. G16H 20/10 600/595 |
| 2014/0316305 A1 | 10/2014 | Venkatraman et al. |
| 2016/0342906 A1 | 11/2016 | Shaashua et al. |
| 2017/0091419 A1* | 3/2017 | Hoglund ............ G16H 20/13 |

OTHER PUBLICATIONS

Mougiakakou et al., "Neural Network based Glucose—Insulin Metabolism Models for Children with Type 1 Diabetes", Proceedings of the 28th IEEE Eng Med Biol Soc. International Conference, Aug. 30-Sep. 3, 2006, pp. 3545-3548.
International Patent Application No. PCT/CA2018/051213, International Search Report dated Jan. 4, 2019, 12 pages.
International Patent Application No. PCT/CA2018/051213, Written Opinion dated Jan. 4, 2019, 4 pages.
Great Britain Patent Appication No. GB2209969.1 Examination Report dated Oct. 3, 2022, 2 pages.
Great Britain Patent Appication No. GB2209969.1 Search Report dated Oct. 2, 2022, 1 page.
Li, et al.; "Smartphone-based personalized blood glucose prediction", ScienceDirect, vol. 2, Issue 4, Oct. 25, 2016, pp. 150-154.
Chemlal, et al.; "Blood Glucose Individualized Prediction for Type 2 Diabetes using iPhone Application", IEEE, 2011 (Conference Apr. 1-3, 2011 and added to IEEE Xplore May 27, 2011), 2 pages.

* cited by examiner

300

Blood glucose record

302 ~ Blood glucose     170
304 ~ Time     12:25 pm, October 5, 2017

340

Heart rate record

342 ~ Heart rate     83
344 ~ Time     12:24 pm, October 5, 2017

410

Recently sensed blood glucose record

| | | |
|---|---|---|
| 412 — | Blood glucose 1 | 203 |
| 413 — | Time | 12:05 pm, October 5, 2017 |
| 414 — | Blood glucose 2 | 195 |
| 415 — | Time | 12:10 pm, October 5, 2017 |
| 416 — | Blood glucose 3 | 186 |
| 417 — | Time | 12:15 pm, October 5, 2017 |
| 418 — | Blood glucose 4 | 178 |
| 419 — | Time | 12:20 pm, October 5, 2017 |
| 420 — | Blood glucose 5 | 170 |
| 421 — | Time | 12:25 pm, October 5, 2017 |

Patient state record

| | | |
|---|---|---|
| 432 — | State ID | Awake |
| 434 — | Heart rate lower bound | 63 |
| 436 — | Heart rate upper bound | 999 |
| 438 — | State ID | Asleep |
| 440 — | Heart rate lower bound | 0 |
| 442 — | Heart rate upper bound | 63 |

FIG. 8

460 

Blood glucose trend record

| | | |
|---|---|---|
| 461 — | Trend ID | 201708051435 |
| 463 — | State ID | Awake |
| 462 — | Blood glucose value 1 | 190 |
| 464 — | Time | 2:35 pm, August 5, 2017 |
| | Blood glucose value 2 | 182 |
| | Time | 2:40 pm, August 5, 2017 |
| | Blood glucose value 3 | 174 |
| | Time | 2:45 pm, August 5, 2017 |
| | Blood glucose value 4 | 166 |
| | Time | 2:50 pm, August 5, 2017 |
| 466 — | Blood glucose value 5 | 158 |
| | Time | 2:55 pm, August 5, 2017 |
| | Blood glucose value 6 | 151 |
| | Time | 3:00 pm, August 5, 2017 |
| | Blood glucose value 7 | 144 |
| | Time | 3:05 pm, August 5, 2017 |
| | ⋮ | ⋮ |
| | Blood glucose value 16 | 100 |
| | Time | 3:50 pm, August 5, 2017 |
| 476 — | Blood glucose value 17 | 98 |
| | Time | 3:55 pm, August 5, 2017 |

Blood glucose trend comparison

| | Trend ID | 201708051435 |
|---|---|---|
| 646 — | Comparison value | 27.75 |

┌─────────────────────────────────────────────────────────┐
│ Determine a change over time of blood glucose levels in the │—702
│ considered blood glucose level trend │
└─────────────────────────────────────────────────────────┘
                              ↓
┌─────────────────────────────────────────────────────────┐
│ Apply a probability function to the change              │—704
└─────────────────────────────────────────────────────────┘
                              ↓
┌─────────────────────────────────────────────────────────┐
│ Determine the weight based on the determined            │—706
│ probability density                                      │
└─────────────────────────────────────────────────────────┘

Blood glucose change distribution record

| | | |
|---|---|---|
| 744 ~ | Time period | 0 |
| 746 ~ | Mean | -5 |
| 748 ~ | Variance | 5 |
| 750 ~ | Time period | 1 |
| | Mean | -6 |
| | Variance | 5 |
| | ⋮ | ⋮ |
| 760 ~ | Time period | 12 |
| 762 ~ | Mean | -10 |
| 764 ~ | Variance | 30 |
| | ⋮ | ⋮ |

Blood glucose trend comparison

| | | |
|---|---|---|
| | Trend ID | 201708051435 |
| 646 ~ | Comparison value | 8368.8 |

Forecast blood glucose change record

| | | |
|---|---|---|
| 802 ~ | Blood glucose change 1 | -10 |
| 804 ~ | Time | 5 minutes |
| | Blood glucose change 2 | -19 |
| | Time | 10 minutes |
| | Blood glucose change 3 | -22 |
| | Time | 15 minutes |
| | Blood glucose change 4 | -30 |
| | Time | 20 minutes |
| | ⋮ | ⋮ |
| | Blood glucose change 12 | -71 |
| | Time | 60 minutes |

Forecast blood glucose record

| | |
|---|---|
| Blood glucose 1 | 160 |
| Time | 12:30 pm, October 5, 2017 |
| Blood glucose 2 | 151 |
| Time | 12:35 pm, October 5, 2017 |
| Blood glucose 3 | 148 |
| Time | 12:40 pm, October 5, 2017 |
| Blood glucose 4 | 140 |
| Time | 12:45 pm, October 5, 2017 |
| ⋮ | ⋮ |
| Blood glucose 12 | 99 |
| Time | 1:25 pm, October 5, 2017 |

Blood glucose trend record

| | | |
|---|---|---|
| | Trend ID | 201706221510 |
| 1002 ∼ | State ID | NULL |
| | Blood glucose value 1 | 220 |
| | Time | 3:10 pm, June 22, 2017 |
| | Blood glucose value 2 | 219 |
| | Time | 3:15 pm, June 22, 2017 |
| | ⋮ | ⋮ |
| | Blood glucose value 17 | 175 |
| | Time | 4:30 pm, June 22, 2017 |

Blood glucose trend record

| | | |
|---|---|---|
| | Trend ID | 201706221510 |
| 1002 ∼ | State ID | Awake |
| | Blood glucose value 1 | 220 |
| | Time | 3:10 pm, June 22, 2017 |
| | Blood glucose value 2 | 219 |
| | Time | 3:15 pm, June 22, 2017 |
| | ⋮ | ⋮ |
| | Blood glucose value 17 | 175 |
| | Time | 4:30 pm, June 22, 2017 |

FIG. 22

1400 

Blood glucose change distribution record

| | |
|---|---|
| 1402 — Time period | 12 |
| BG change 1 probability | −390 to −360 mg/dL per hour 0.0005 |
| BG change 2 probability | −360 to −330 mg/dL per hour 0.0005 |
| ⋮ | |
| BG change 26 probability | 360 to 390 mg/dL per hour 0.0005 |

FIG. 25

1460 

Probability density correction record

| | |
|---|---|
| BG change 1 Probability correction | −390 to −360 mg/dL per hour 0.000025 |
| BG change 2 Probability correction | −360 to −330 mg/dL per hour 0.000025 |
| ⋮ | |
| BG change 26 Probability correction | 360 to 390 mg/dL per hour 0.000025 |

Activity record

| | | |
|---|---|---|
| 1302 — | Activity | 0.00300 |
| 1304 — | Time | 12:35 pm, October 5, 2017 |

Patient state record

| | | |
|---|---|---|
| 1342 — | State ID | Awake and active (Sport) |
| 1344 — | Heart rate lower bound | 112 |
| 1346 — | Heart rate upper bound | 999 |
| 1348 — | Activity lower bound | 0.3 |
| 1350 — | Activity upper bound | 999 |
| 1352 — | State ID | Elevated heart rate inactive |
| | Heart rate lower bound | 112 |
| | Heart rate upper bound | 999 |
| | Activity lower bound | 0 |
| | Activity upper bound | 0.3 |
| 1360 — | State ID | Awake and inactive |
| | Heart rate lower bound | 63 |
| | Heart rate upper bound | 112 |
| | Activity lower bound | 0 |
| | Activity upper bound | 0.3 |
| 1370 — | State ID | Awake and active (low hr) |
| | Heart rate lower bound | 63 |
| | Heart rate upper bound | 112 |
| | Activity lower bound | 0.3 |
| | Activity upper bound | 999 |
| 1380 — | State ID | Asleep |
| | Heart rate lower bound | 0 |
| | Heart rate upper bound | 63 |
| | Activity lower bound | 0 |
| | Activity upper bound | 0.01 |
| 1390 — | State ID | Sleep (About to wake up) |
| | Heart rate lower bound | 0 |
| | Heart rate upper bound | 63 |
| | Activity lower bound | 0.01 |
| | Activity upper bound | 999 |

FIG. 31

PHYSIOLOGICAL PROPERTY FORECASTING

CROSS REFERENCE TO RELATED APPLICATION

This application is a National Stage of International Application No. PCT/CA2018/051213 filed on Sep. 26, 2018, which claims the benefit of U.S. Application No. 62/614,047 filed on Jan. 5, 2018, and claims the benefit of U.S. Application No. 62/563,078, filed on Sep. 26, 2017, all of which are hereby incorporated by reference in their entireties.

BACKGROUND

1. Field

Embodiments of this invention relate to monitoring physiology and more particularly to physiological property forecasting for detecting disease complications.

2. Description of Related Art

Patients and clinicians may use computers and computer systems to monitor physiological properties of patients. For example, known computers may be configured to monitor blood glucose levels to help manage insulin-dependent diabetes mellitus. While some known computers may attempt to predict future blood glucose levels of patients, these predictions do not consider various factors which may be indicative of how physiological properties evolve over time. For example, some computers do not consider what state a patient is in before predicting a future physiological property. Accordingly, some known computers will be incorrect and/or inaccurate with predictions of physiological properties.

SUMMARY

In accordance with one embodiment, there is provided a computer-implemented method of facilitating physiological property forecasting and for detecting disease complications. The method involves receiving signals representing sensed physiological property indicators, each of the sensed physiological property indicators representing a sensed physiological property of a patient at a respective time and receiving signals representing one or more contextual indicators associated with the sensed physiological property indicators. The method also involves applying at least one classification criterion to the one or more contextual indicators to determine a patient state of a plurality of possible patient states, each patient state associated with a respective set of forecasting parameters and applying the set of forecasting parameters associated with the determined patient state to the sensed physiological property indicators to determine at least one forecast physiological property indicator representing a forecast physiological property of the patient at a future time.

In accordance with another embodiment, there is provided a computer-implemented method of facilitating physiological property forecasting for detecting disease complications, the method involving causing at least one processor to perform the above method.

In accordance with another embodiment, there is provided a system for facilitating physiological property forecasting for detecting disease complications, the system including at least one processor configured to execute the above method.

In accordance with another embodiment, there is provided a computer readable medium having stored thereon codes which when executed by at least one processor cause the at least one processor to perform the above method.

In accordance with another embodiment, there is provided a system for facilitating physiological property forecasting for detecting disease complications. The system includes provisions for receiving signals representing sensed physiological property indicators, each of the sensed physiological property indicators representing a sensed physiological property of a patient at a respective time and provisions for receiving signals representing one or more contextual indicators associated with the sensed physiological property indicators. The system also includes provisions for applying at least one classification criterion to the one or more contextual indicators to determine a patient state of a plurality of possible patient states, each patient state associated with a respective set of forecasting parameters and provisions for applying the set of forecasting parameters associated with the determined patient state to the sensed physiological property indicators to determine at least one forecast physiological property indicator representing a forecast physiological property of the patient at a future time.

Other aspects and features of embodiments of the invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 7 is a representation of an exemplary recently sensed blood glucose record that may be used in the system shown in FIG. 1;

FIG. 8 is a representation of an exemplary patient state record that may be used in the system shown in FIG. 1;

FIG. 9 is a representation of an exemplary blood glucose trend record that may be used in the system shown in FIG. 1;

FIG. 12 is a representation of an exemplary blood glucose trend comparison record that may be used in the system shown in FIG. 1;

FIG. 13 is a flowchart depicting blocks of code that may be included in the flowchart of FIG. 11 in accordance with various embodiments of the invention;

FIG. 14 is a representation of an exemplary blood glucose change distribution record that may be used in the system shown in FIG. 1;

FIG. 15 is a representation of an exemplary blood glucose trend comparison record that may be used in the system shown in FIG. 1;

FIG. 16 is a representation of an exemplary forecast blood glucose change record that may be used in the system shown in FIG. 1;

FIG. 17 is a representation of an exemplary forecast blood glucose record that may be used in the system shown in FIG. 1;

FIG. 21 is a representation of an exemplary blood glucose trend record that may be used in the system shown in FIG. 1;

FIG. 22 is a representation of an exemplary blood glucose trend record that may be used in the system shown in FIG. 1;

FIG. 25 is a representation of an exemplary blood glucose change distribution record that may be used in the system shown in FIG. 1;

FIG. 26 is a representation of an exemplary probability density correction record that may be used in the system shown in FIG. 1;

FIG. 30 is a representation of an exemplary activity record that may be used in the system shown in FIG. 27;

FIG. 31 is a representation of an exemplary patient state record that may be used in the system shown in FIG. 27.

DETAILED DESCRIPTION

Figure 1:
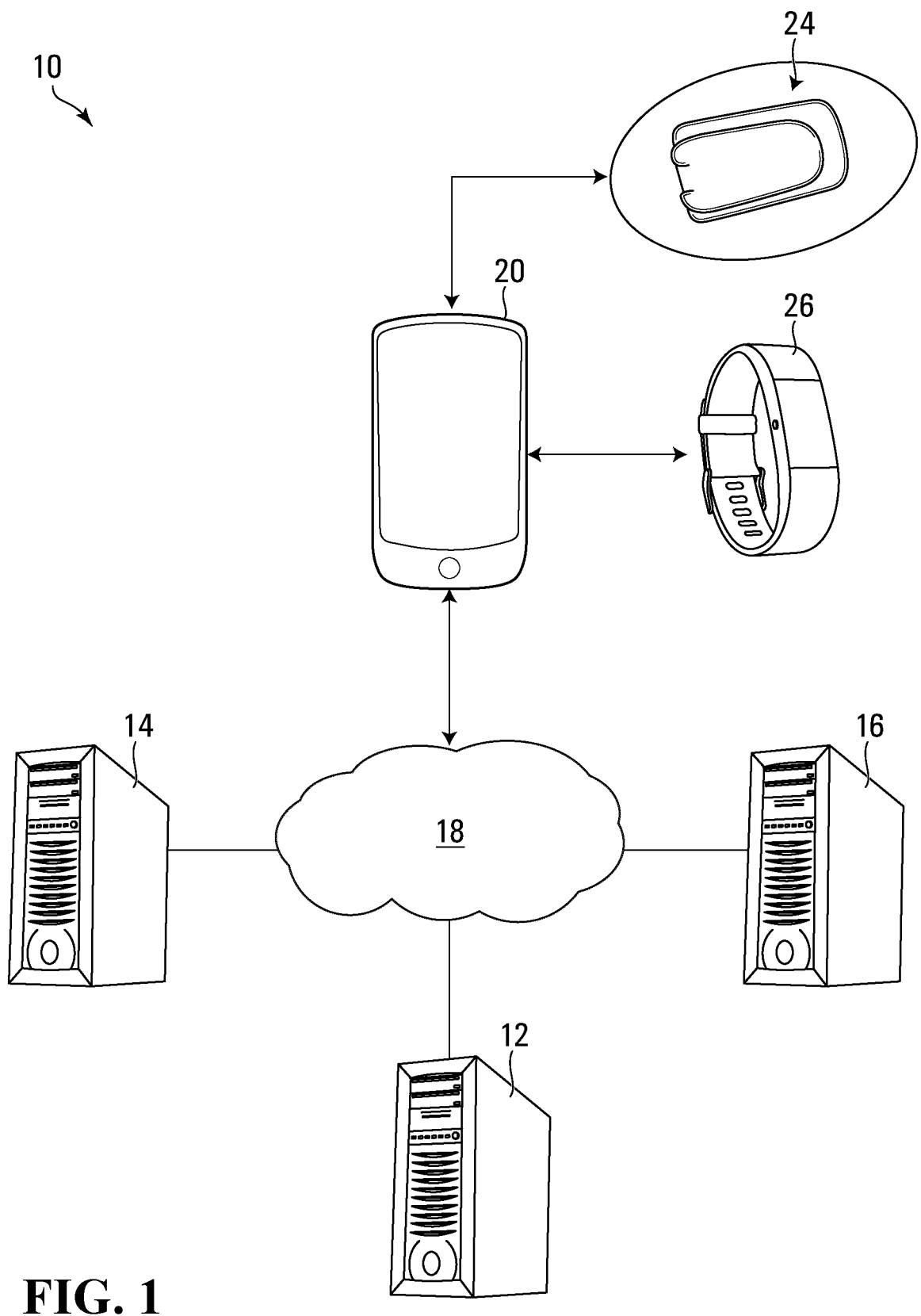
FIG. 1 is a schematic view of a system for facilitating physiological property forecasting for detecting disease complications in accordance with various embodiments of the invention.

In various embodiments of the invention described herein, computer-implemented monitoring of physiological properties and/or forecasting future physiological properties of a patient may be helpful for improving health and/or preventing dangerous conditions from arising. For example, a patient or clinician may wish to use a computer or computer system to monitor physiological properties that may indicate a severe health event such as disease complications, a medical condition, and/or a potential medical problem, for example. Some examples of physiological properties that may be monitored include blood glucose levels, blood pressure, heart rate, electrocardiographic data, body temperature, and/or blood oxygen saturation (SPO2), for example.

In various embodiments, information regarding blood glucose levels may facilitate detection and/or prediction of hypoglycemia and hyperglycemia, blood pressure may facilitate detection and/or prediction of cardiovascular problems, heart rate may facilitate detection and/or prediction of cardiovascular problem palpitation, infection, and/or arrhythmia, body temperature may facilitate detection and/or prediction of infection, and blood oxygen may facilitate detection and/or prediction of an asthma attack and/or a lung condition.

In various embodiments, it may be especially desirable for the computer or computer system to forecast future physiological properties for a patient. However, configuring a computer to forecast future physiological properties can be difficult as there are many factors which may affect how a patient's physiology will evolve over time.

In various embodiments described herein, a computer system for physiological property forecasting for detecting disease complications may include a computer-implemented forecaster for facilitating physiological property forecasting. The forecaster may be configured to use contextual information associated with sensed physiological properties to improve accuracy in forecasting future physiological properties for a patient. In various embodiments, the contextual information may be used to determine a state that the patient is in and the state that the patient is in may be indicative of how the physiological properties of the patient can be expected to change over time based on the patient's physiological state. Accordingly, by analyzing contextual information, the forecaster may be able to determine a state of the patient and thereby better forecast or predict future physiological properties for the patient.

In some embodiments, knowing a patient state may be particularly useful for forecasting future physiological properties when the patient state is associated with different expectations for how the physiological properties will evolve.

In some embodiments, the contextual information may include physiological properties different from the physiological properties that the patient/clinician wishes to forecast and/or monitor. For example, in some embodiments, the contextual information may include heart rate information, such as, sensed heart rate information. The sensed heart rate information may provide near real time context, which may be indicative of a state that the patient is in, which may in turn be indicative of how physiological properties of the patient may be mathematically modeled and used to forecast. For example, in various embodiments, heart rate information may provide information directly relevant to how blood glucose levels in a patient can be modeled. For example, in some embodiments, the sensed heart rate information may be used to determine whether the patient is in an "Awake" or in an "Asleep" state which may be associated with different expectations in how blood glucose levels will change for the patient over time.

In some embodiments, patient states may include an "Awake" state and an "Asleep" state, since these states may correspond to very different progressions in physiological properties. In various embodiments, for example, blood glucose levels may be expected to decrease more slowly when the patient is asleep than when the patient is awake. Since the different states may be indicative of how the physiological properties of the patient will change over time, each of the states may be associated with different forecasting parameters, which can be applied to forecast physiological properties of the patient at future times.

In some embodiments, heart rate information may be used to determine whether the patient is in additional or alternative states, such as, for example, "High stress" or "Playing Sports", which may each be associated with different progressions in physiological properties, such as blood glucose levels.

In some embodiments, the contextual information may further or alternatively include other information about the patient and/or the physiological properties which are to be forecast. For example, in some embodiments, the contextual information may include activity information for the patient since activity of the patient may be indicative of a state the patient is in and may be relevant to how the patient's physiological properties will change over time. For example, the activity information could help determine what the patient is doing, such as being active by, jogging, for example, or being inactive by, taking a rest or a nap, for example.

In some embodiments, the contextual information may include blood oxygen saturation levels, which may be used to determine whether the patient is in an "Awake and active (Sport)" state, "Awake and inactive" state, "Awake and elevated (Stressed/sickness)" state, "In Pain" state, "Deep sleep" state, and/or "Sleep (about to wake up)" state, for example.

In some embodiments, the contextual information may include body temperature information, which may be used to determine whether the patient is in an "Infection" state. Body temperature may also or alternatively be used to determine whether the patient is in a "Drug use" state. Body temperature may also or alternatively be used to determine whether a female patient is in a patient state associated with a beginning, middle or end of their menstrual cycle, for example.

In some embodiments, the contextual information may include blood pressure information which may be used to determine whether the patient is in a variety of cardio vascular states.

In operation, the forecaster may be configured to receive sensed physiological property indicators, each representing a sensed physiological property of a patient at a respective time. For example, in some embodiments described herein, the sensed physiological property may be a blood glucose level of the patient and the forecaster may be configured to receive sensed blood glucose values representing the blood glucose levels of the patient and associated time values representing times at which the blood glucose values were sensed. The forecaster may be configured to also receive contextual indicators associated with the sensed physiological property indicators. For example, in some embodiments described herein, the forecaster may be configured to receive heart rate values representing heart rates of the patient at the times the blood glucose levels were sensed.

The forecaster may be configured to apply at least one classification criterion to the contextual indicators to determine a patient state of a plurality of possible patient states, each patient state associated with a respective set of forecasting parameters. For example, where the contextual indicators include heart rate values, the forecaster may be configured to apply heart rate range criteria to the heart rate values to determine whether an average of the heart rate values is within a particular range that is associated with a patient state of "Awake" or within another range that is associated with a patient state of "Asleep". Each of the patient states "Awake" and "Asleep" may be associated with forecasting parameters in computer memory accessible by the forecaster.

The forecaster may be configured to apply the set of forecasting parameters associated with the determined patient state to the sensed physiological property indicators to determine at least one forecast physiological property indicator representing a forecast physiological property of the patient at a future time. For example, in various embodiments, the forecaster may be configured to retrieve forecasting parameters from the computer memory which are associated with the state determined and to generate a function based on the retrieved forecasting parameters, the function providing physiological properties as a function of time. In some embodiments, the forecaster may be configured to use the function to determine one or more forecast physiological properties of the patient at a future time.

In various embodiments, the forecaster may be configured to produce signals for causing at least one display to display the determined one or more forecast physiological properties to the patient and/or a clinician, for example. The patient and/or clinician may evaluate the displayed forecast physiological properties and may take action if they deem it necessary.

Referring now to FIG. 1, there is provided a system 10 for physiological property forecasting in accordance with an embodiment. The system 10 shown in FIG. 1 may be configured for blood glucose level forecasting. For example, a patient may wish to monitor their blood glucose level to help manage insulin-dependent diabetes mellitus and the patient or a clinician may use the system 10 to estimate current blood glucose levels and/or to forecast or predict future blood glucose levels. In some embodiments, the system 10 may be configured to provide information that reveals where a patient's blood glucose level is, where the blood glucose level is heading, and/or how fast it is changing. In various embodiments, this information may allow a patient and/or clinician to take proactive action, such as, eating food, administering an insulin injection, or taking some other corrective measures, for example, to help avoid dangerously low or high blood glucose levels.

In the embodiment shown, the system 10 includes a forecaster 12 for facilitating physiological property forecasting. The system 10 also includes a blood glucose sensor 24 acting as a physiological property sensor for sensing blood glucose levels of a patient and a heart rate sensor 26 for sensing the patient's heart rate. The forecaster 12 may be configured to use sensed heart rates of the patient as contextual information for helping to facilitate blood glucose level forecasting.

In some embodiments, using the patient's heart rate as contextual information may facilitate improved accuracy in determining states of the patient. In some embodiments, heart rate information may be indicative of patient states that are useful for predicting or forecasting blood glucose levels and so using heart rate information as contextual information may facilitate improved forecasting for blood glucose levels.

Referring still to FIG. 1, in operation, a patient may have installed the blood glucose sensor 24, such as by insertion in the patient and the blood glucose sensor 24 may be configured to sense blood glucose levels over time. In some embodiments, the blood glucose sensor 24 may include a continuous glucose monitor (CGM). The blood glucose sensor 24 may be configured to make blood glucose information available to the forecaster 12 such that the forecaster 12 can analyze blood glucose levels over time and provide a forecast of one or more future blood glucose levels for the patient. The blood glucose information may include sensed blood glucose values representing sensed blood glucose levels of the patient and associated times or time period information representing times or time periods at which the blood glucose levels were sensed.

In some embodiments, due to technical limitations, privacy and/or data management concerns, one or more intermediaries may be included in the system 10 for communicating the blood glucose information from the blood glucose sensor 24 to the forecaster 12. For example, referring to FIG. 1, the blood glucose sensor 24 may not be capable of communicating or permitted to communicate with the forecaster 12 directly. Accordingly, the blood glucose sensor 24 may use one or more intermediaries to provide blood glucose information to the forecaster 12.

For example, referring to FIG. 1, the system 10 includes a patient device 20 in communication with the blood glucose sensor 24 and a network 18, which may include one or more intranets and/or the Internet, for example. In various embodiments, the patient device 20 may include any of a variety of computing devices configured to facilitate communications through the network 18 of data sensed by the sensors 24 or 26. For example, in some embodiments, the patient device 20 may include a smartphone, a tablet, a personal computer, a laptop, or another form of computing device capable of communication via the network 18. In some embodiments, the patient device 20 may include a display and/or a graphical user interface for providing information for a patient or clinician using the system 10.

In various embodiments, the system 10 may also include a blood glucose data source 14 in communication with the patient device 20 and the forecaster 12 via the network 18. The blood glucose data source 14 may include a server computer or computer system in communication with the network 18. In various embodiments, the blood glucose data source 14 may be managed or controlled by the entity that manufactures the blood glucose sensor 24 and/or may have permissions for directly receiving and managing information sensed by the blood glucose sensor 24, whereas the forecaster 12 may not, and so the blood glucose data source 14 may act as an intermediary for providing the blood glucose information to the forecaster 12.

In various embodiments, the blood glucose sensor 24 may be configured to transmit blood glucose information to the forecaster 12 via the patient device 20, the network 18, and the blood glucose data source 14. The blood glucose sensor 24 may be configured to transmit the blood glucose information to the patient device 20 via a communication link, such as for example, through wireless communication (e.g. Bluetooth™ wireless communication, for example), and the patient device 20 may be configured to receive the blood glucose information and to send the blood glucose information to the blood glucose data source 14 via a communication link, such as for example, through a wireless connection (e.g. a mobile device data connection, such as a 4G connection, for example) with the network 18. The blood glucose data source 14 may be configured to receive the blood glucose information and to send the blood glucose information to the forecaster 12.

In some embodiments, the heart rate sensor 26 may include or be incorporated in an activity tracking device, for example, configured to monitor heart rate and/or activity levels. Referring still to FIG. 1, in various embodiments, a patient may install the heart rate sensor 26, such as, for example, by wearing the sensor on their wrist, and the sensor 26 may be configured to sense a heart rate of the patient over time. The sensor 26 may be configured to transmit heart rate information to the forecaster 12 such that the forecaster 12 can use this information as contextual information to help with forecasting one or more future blood glucose levels for the patient. The heart rate information may include sensed heart rate values representing heart rates and associated time or time period information representing times or time periods at which the heart rates were sensed.

In some embodiments, for example, for generally similar reasons to those provided above regarding the blood glucose information sensed by the blood glucose sensor 24, the heart rate information may be transmitted from the heart rate sensor 26 to the forecaster 12 through one or more intermediaries. Accordingly, in various embodiments, the system 10 may include a heart rate data source 16, and the patient device 20 and the heart rate data source 16 may act as intermediaries for receiving the heart rate information and transmitting it to the forecaster 12, generally as described above regarding the blood glucose information.

In view of the foregoing, blood glucose information acting as physiological property information and heart rate information acting as contextual information may be transmitted to the forecaster 12.

In operation, the forecaster 12 may receive the blood glucose information including blood glucose values and associated time information from the blood glucose data source 14. The forecaster 12 may also receive the heart rate information including heart rate values and associated time information from the heart rate data source 16. In various embodiments, sensed blood glucose values and sensed heart rate values may be considered associated when they are associated with corresponding or common times or time periods.

The forecaster 12 may apply at least one classification criterion to the sensed heart rate values to determine a patient state of a plurality of possible patient states, each patient state associated with a respective set of forecasting parameters. For example, in some embodiments, patient states may include "Awake" and "Asleep" and each of the patient states "Awake" and "Asleep" may be associated with a respective set of forecasting parameters. The forecaster 12 may be configured to determine that the patient is in the "Awake" patient state when sensed heart rates are higher than a threshold heart rate and that the patient is in the "Asleep" state when the sensed heart rates are lower than the threshold heart rate.

The forecaster 12 may apply the set of forecasting parameters associated with the determined patient state to the sensed blood glucose values to determine at least one forecast blood glucose value representing an expected or predicted blood glucose level at a future time. For example, in some embodiments, each set of forecasting parameters may include a plurality of sets of historical blood glucose values, each of the sets of historical blood glucose values representing blood glucose levels of the patient during a respective historical time period.

In some embodiments, the forecaster 12 may apply the forecasting parameters by comparing the sensed blood glucose values to each of the sets of historical blood glucose values included in the forecasting parameters associated with the determined patient state, selecting at least one of the sets of historical blood glucose values based on the comparison, generating a time-dependent function representing the selected sets of historical blood glucose values, and determining the at least one forecast blood glucose value using the function.

In some embodiments, after the at least one forecast blood glucose value has been determined, the forecaster 12 may send the at least one forecast blood glucose value to the patient device 20 via the network 18 and the patient device 20 may display the at least one forecast blood glucose value to the patient and/or clinician for their review and consideration.

Forecaster—Processor Circuit

Figure 2:
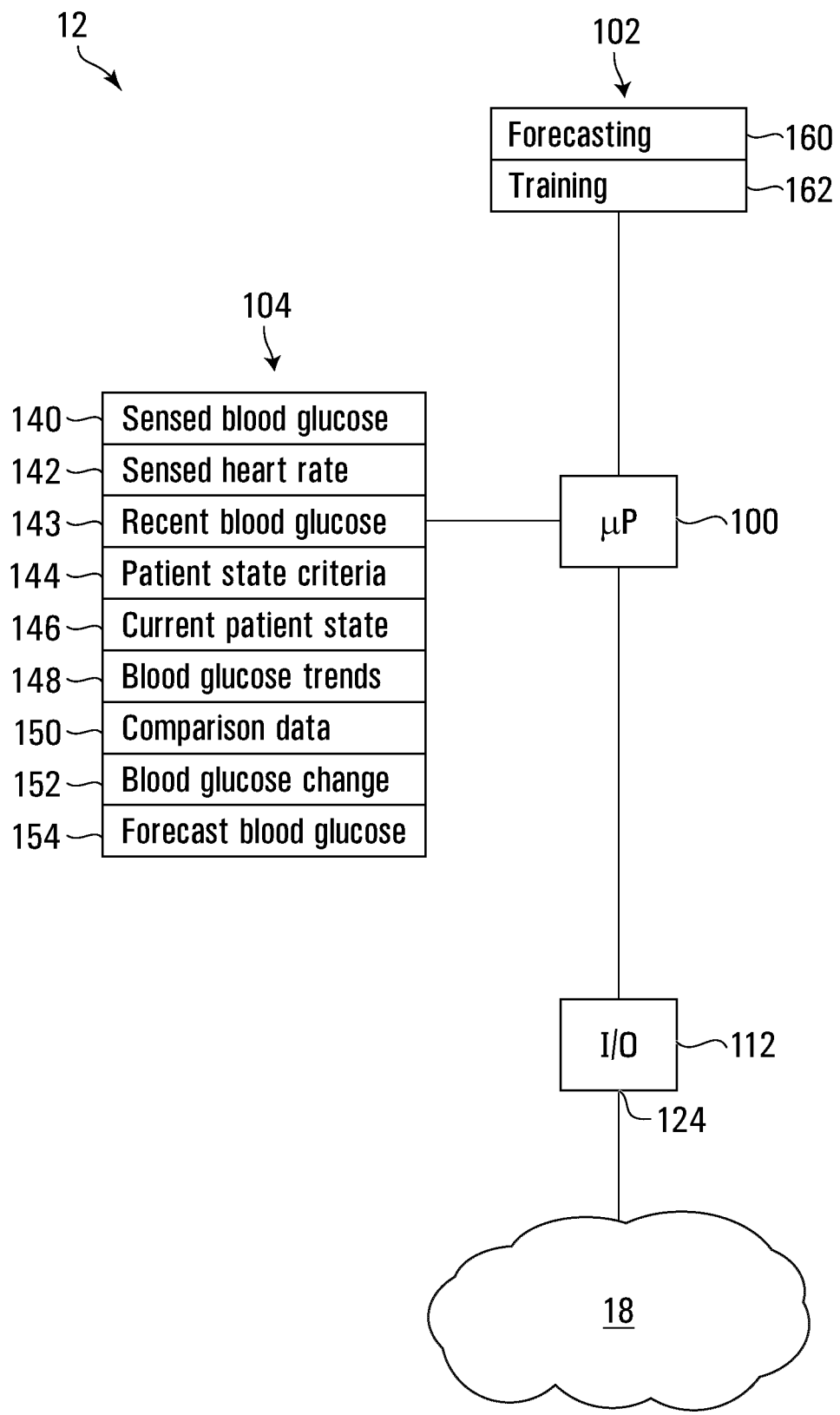
FIG. 2 is a schematic view of a forecaster shown in the system of FIG. 1 including a processor circuit in accordance with various embodiments of the invention.

Referring now to FIG. 2, a schematic view of the forecaster 12 of the system 10 shown in FIG. 1 according to an embodiment is shown. Referring to FIG. 2, the forecaster 12 includes a processor circuit including a forecaster processor 100 and a program memory 102, a storage memory 104, and an input/output (I/O) interface 112, all of which are in communication with the forecaster processor 100. In various embodiments, the forecaster processor 100 may include one or more processing units, such as for example, a central processing unit (CPU), a graphical processing unit (GPU), and/or a processor circuit accessible using an Application Programming Interface (API). In some embodiments, any or all of the functionality of the forecaster 12 described herein may be implemented using a processing circuit accessible via one or more APIs.

The I/O interface 112 includes an interface 124 for facilitating networked communication through the network 18. In some embodiments, the interface 124 may facilitate wireless or wired communication. In some embodiments, the I/O interface 112 may include a network interface device or card with an input/output for connecting to the network 18, through which communications may be conducted with devices connected to the network 18, such as the blood glucose data source 14, heart rate data source 16, and the patient device 20 shown in FIG. 1, for example. In some embodiments, the interface 124 may include one or more interfaces.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the forecaster processor 100 to carry out various functions are stored in the program memory 102. Referring to FIG. 2, the program memory 102 includes a block of codes 160 for directing the forecaster 12 to perform forecasting functions and a block of codes 162 for directing the forecaster processor 100 to perform training functions. In this specification, it may be stated that certain encoded entities such as applications or modules perform certain functions. Herein, when an application, module or encoded entity is described as taking an action, as part of, for example, a function or a method, it will be understood that at least one processor (e.g. the forecaster processor 100) is directed to take the action by way of programmable codes or processor-executable codes or instructions defining or forming part of the application.

The storage memory 104 includes a plurality of storage locations including location 140 for storing sensed blood glucose information, location 142 for storing sensed heart rate information, location 143 for storing recent blood glucose information, location 144 for storing patient state criteria information, location 146 for storing current patient state information, location 148 for storing blood glucose trend information, location 150 for storing comparison information, location 152 for storing blood glucose change information, and location 154 for storing forecast blood glucose information. In various embodiments, the plurality of storage locations may be stored in a database in the storage memory 104.

In various embodiments, the blocks of codes 160 and 162 may be integrated into a single block of codes and/or each of the blocks of code 160 and 162 may include one or more blocks of code stored in one or more separate locations in program memory 102. In various embodiments, any or all of the locations 140, 142, 143, 144, 146, 148, 150, 152, and 154 may be integrated and/or each may include one or more separate locations in the storage memory 104.

In various embodiments, each of the program memory 102 and storage memory 104 may be implemented as one or more storage devices including, for example, random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the forecaster 12 and in communication with the forecaster 12 via the I/O interface 112, for example.

Forecasting

Figure 3:
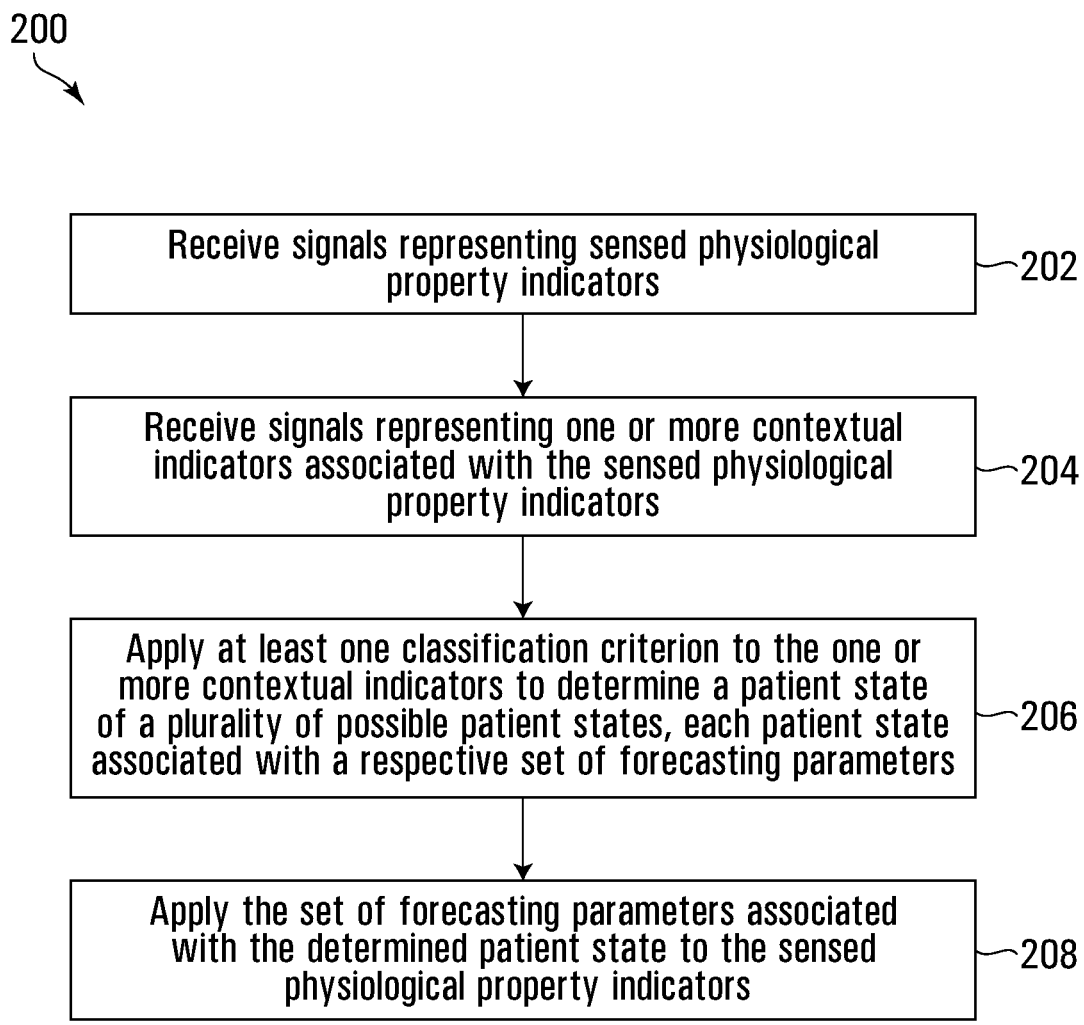
FIG. 3 is a flowchart depicting blocks of code for directing the forecaster of the system of FIG. 1 to perform forecasting functions in accordance with various embodiments of the invention.

Referring now to FIG. 3, a flowchart depicting blocks of code for directing the forecaster processor 100 shown in FIG. 2 to perform forecasting functions in accordance with one embodiment is shown generally at 200. The blocks of code included in the flowchart 200 may be encoded in the block of codes 160 of the program memory 102 shown in FIG. 2, for example.

Flowchart 200 may be executed when a patient or clinician wishes to forecast or predict one or more future physiological properties of the patient, based on sensed physiological properties and contextual information. For example, in some embodiments the flowchart 200 may be executed when a patient or clinician wishes to forecast future blood glucose levels based on sensed blood glucose levels and sensed heart rates of the patient.

In some embodiments, the patient device 20 may be configured to provide a graphical user interface (GUI) to the patient via a display of the patient device 20. The patient may interact with the GUI to cause the patient device 20 to transmit a request to forecast future physiological properties to the forecaster 12 via the network 18. The forecaster 12 may be configured to receive the request via the I/O interface 112 and to cause the flowchart 200 to be executed in response to receiving the request.

Referring to FIG. 3, the flowchart 200 begins with block 202 which directs the forecaster processor 100 shown in FIG. 2 to receive signals representing sensed physiological property indicators, each of the sensed physiological property indicators representing a sensed physiological property of a patient at a respective time.

In some embodiments, blood glucose values representing blood glucose levels sensed by the blood glucose sensor 24 shown in FIG. 1 may be sent to the forecaster 12 via the patient device 20, the network 18, and the blood glucose data source 14. The blood glucose values may act as physiological property indicators and block 202 may direct the forecaster processor 100 to receive signals representing the blood glucose values via the interface 124 of the I/O interface 112 shown in FIG. 2 from the blood glucose data source 14. For example, in various embodiments, block 202 may direct the forecaster processor 100 to request and receive a JSON representation of blood glucose values and associated times at which blood glucose levels represented by the blood glucose values were sensed, via the interface 124 of the I/O interface 112 shown in FIG. 2.

Block 202 may direct the forecaster processor 100 to store representations of the received blood glucose values and associated times in the storage memory 104. For example, in some embodiments, block 202 may direct the forecaster processor 100 to store a plurality of blood glucose records representing the received blood glucose values and associated times in the location 140 of the storage memory 104.

Figure 4:
FIG. 4 is a representation of an exemplary blood glucose record that may be used in the system shown in FIG. 1.

An exemplary blood glucose record 300 is shown in FIG. 4. Referring to FIG. 4, the blood glucose record 300 includes a blood glucose field 302 for storing a blood glucose value representing a blood glucose level in the patient. For example, in some embodiments, the blood glucose field may store a numerical blood glucose value representing a blood glucose level of the patient in mg/dL. The blood glucose record 300 also includes a time field 304 for storing a time value representing a date and time at which the blood glucose level represented by the value stored in the blood glucose field 302 was sensed. In various embodiments, the time value stored in the time field 304 may be stored as a Unix timestamp value.

Block 202 of the flowchart 200 shown in FIG. 3 may direct the forecaster processor 100 to generate a blood glucose record having format generally the same as the blood glucose record 300 shown in FIG. 4, for each blood glucose value and associated time value received at block 202. In some embodiments, block 202 may be executed multiple times and/or continuously as blood glucose values and associated time values are received from the blood glucose data source 14 shown in FIG. 1, for example. In some embodiments, the blood glucose values and associated time values may be received in near real time as they are measured at the patient. After code included in block 202 has been executed, there may be a plurality of blood glucose records stored in the location 140 of the storage memory 104, each of the stored blood glucose records representing a blood glucose level of the patient at a respective time.

Block 204 of the flowchart 200 shown in FIG. 3 then directs the forecaster processor 100 shown in FIG. 2 to receive signals representing one or more contextual indicators associated with the sensed physiological property indicators. In some embodiments, heart rate values representing heart rates sensed by the sensor 26 shown in FIG. 1 may be sent to the forecaster 12 via the patient device 20, the network 18, and the heart rate data source 16. In various embodiments, the heart rate values may act as contextual indicators and block 204 may direct the forecaster processor 100 to receive signals representing the heart rate values via the interface 124 of the I/O interface 112 shown in FIG. 2 from the heart rate data source 16. For example, in various embodiments, block 204 may direct the forecaster processor 100 to request and receive JSON representations of heart rate values and associated times at which the heart rates represented by the heart rate values were sensed, via the interface 124 of the I/O interface 112 shown in FIG. 2.

Block 204 of the flowchart 200 shown in FIG. 3 may direct the forecaster processor 100 to store representations of the received heart rate values and associated times in the storage memory 104. For example, in some embodiments, block 204 may direct the forecaster processor 100 to generate and store a plurality of heart rate records representing the received heart rates and associated times in the location 142 of the storage memory 104. An exemplary heart rate record 340 is shown in FIG. 5.

Figure 5:
FIG. 5 is a representation of an heart rate record that may be used in the system shown in FIG. 1.

Referring to FIG. 5, the heart rate record 340 includes a heart rate field 342 for storing a heart rate value representing a heart rate of the patient. In some embodiments, the heart rate field 342 may store a numeric heart rate value that represents the heart rate of the patient in beats per minute. The heart rate record 340 also includes a time field 344 for storing a time value representing the time or time period at which the heart rate was sensed.

In some embodiments, block 204 may be executed multiple times and/or continuously as heart rate values and associated time values are received from the heart rate data source 16 shown in FIG. 1. After code included in block 204 has been executed, there may be a plurality of heart rate records stored in the location 142 of the storage memory 104, each of the stored heart rate records representing a heart rate of the patient at a respective time.

Referring to FIG. 3, block 206 directs the forecaster processor 100 shown in FIG. 2 to apply at least one classification criterion to the one or more contextual indicators to determine a patient state of a plurality of possible patient states, each patient state associated with a respective set of forecasting parameters. In various embodiments, block 206 may direct the forecaster processor 100 to apply classification criteria to the heart rate values included in the heart rate records stored in the location 142 of the storage memory 104.

In some embodiments, block 206 of the flowchart shown in FIG. 3 may direct the forecaster processor 100 shown in FIG. 2 to consider heart rate values representing heart rates associated with recently sensed blood glucose values and determine whether the heart rates represented by the heart rate values are within one of a plurality of ranges, each range associated with a patient state. For example, in some embodiments, block 206 may direct the forecaster processor 100 to determine whether the heart rate values are within a range associated with a patient state of "Awake" or if the heart rate values are within a range associated with a patient state of "Asleep". Each of the patient states, "Awake" and "Asleep", may be associated with a set of forecasting parameters which may be applied at block 208 of the flowchart 200 shown in FIG. 3 as described in further detail below.

Figure 6:
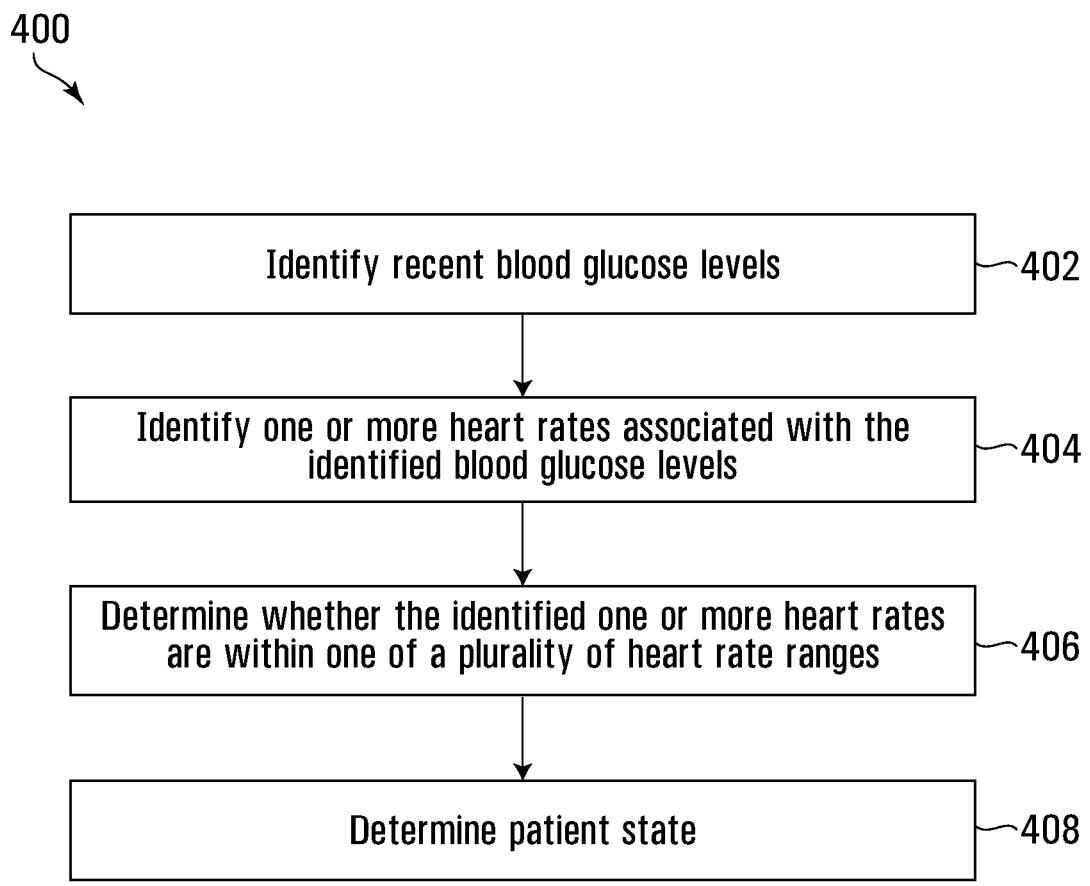
FIG. 6 is a flowchart depicting blocks of code that may be included in the flowchart of FIG. 2 in accordance with various embodiments of the invention.

Referring to FIG. 6, there is provided a flowchart 400 depicting blocks of code which may be included in the block 206 of the flowchart 200 shown in FIG. 3, in accordance with various embodiments. The blocks of code included in the flowchart 400 may direct the forecaster processor 100 to apply classification criteria to representations of recently sensed heart rates of a patient.

The flowchart 400 shown in FIG. 6 begins with block 402, which directs the forecaster processor 100 shown in FIG. 2 to identify one or more recently sensed blood glucose levels which are to be considered for the forecasting. In various embodiments, block 402 may direct the forecaster processor 100 to identify a predetermined number of blood glucose records stored in the location 140 of the storage memory 104 that represent recently sensed blood glucose levels. For example, in some embodiments, block 402 may direct the forecaster processor 100 to read the time fields of the blood glucose records stored in the location 140 of the storage memory 104 to identify blood glucose records which include time values representing the most recent times.

In some embodiments, block 402 may direct the forecaster processor 100 to identify blood glucose records which include time values that represent times within a recent time period. The recent time period may be a time period that is expected to include enough blood glucose records to facilitate forecasting.

In some embodiments, block 402 of the flowchart 400 shown in FIG. 6 may direct the forecaster processor 100 shown in FIG. 2 to identify a predetermined number of blood glucose records, which, based on a known frequency for sensing the blood glucose levels, may represent blood glucose levels for a recent time period. For example, in some embodiments, the blood glucose levels may be sensed or measured at 5-minute intervals and block 402 may direct the forecaster processor 100 to identify the blood glucose records that include time values representing the 5 most recent times, corresponding to 25 minutes of blood glucose level readings. In various embodiments, blood glucose levels over a recent 25-minute time period may facilitate forecasting of blood glucose levels about an hour in the future. In various embodiments, other time periods may be used and additional or fewer blood glucose records may be identified as representing recently sensed blood glucose values at block 402.

Block 402 may direct the forecaster processor 100 to generate a recently sensed blood glucose record 410 shown in FIG. 7 representing the identified recent blood glucose levels and to store the recently sensed blood glucose record 410 in the location 143 of the storage memory 104. Referring to FIG. 7, the recently sensed blood glucose record 410 includes blood glucose fields 412, 414, 416, 418, and 420 for storing blood glucose values and associated respective time fields 413, 415, 417, 419, and 421 for storing associated time values. In various embodiments, block 402 may direct the forecaster processor 100 to set the blood glucose fields and associated time fields of the recently sensed blood glucose record 410 to the blood glucose values and time values of the identified blood glucose records.

Block 404 of the flowchart 400 shown in FIG. 6 then directs the forecaster processor 100 shown in FIG. 2 to identify one or more heart rates associated with the identified blood glucose levels. In various embodiments, block 402 may direct the forecaster processor 100 to identify heart rate records stored in the location 142 of the storage memory 104, which include time values that correspond to a time period represented by the time values of the recently sensed blood glucose record 410 shown in FIG. 7. For example, in some embodiments, block 404 may direct the forecaster processor 100 to identify heart rate records stored in the location 142 of the storage memory 104 that include time values that are greater than the smallest time value included in the recently sensed blood glucose record 410 and less than the largest time value included in the recently sensed blood glucose record 410.

After blocks 402 and 404 of the flowchart 400 shown in FIG. 6 have been executed, the forecaster processor 100 may have identified a plurality of blood glucose values representing recent blood glucose levels of the patient and one or more heart rate values associated with the plurality of blood glucose values and representing heart rates of the patient.

Referring to FIG. 6, block 406 directs the forecaster processor 100 shown in FIG. 2 to determine whether the identified one or more heart rates is within one of a plurality of heart rate ranges. In various embodiments, block 406 may direct the forecaster processor 100 to determine an average heart rate value from the heart rate values of the heart rate records identified at block 404. Block 406 may direct the forecaster processor 100 to compare the average heart rate value to a plurality of heart rate ranges, each associated with a patient state. In some embodiments, using the average heart rate value may facilitate comparisons even when there is missing data for the heart rate and/or the heart rate data is noisy.

In various embodiments, block 406 may direct the forecaster processor 100 to retrieve a patient state record 430 from the location 144 of the storage memory 104 shown in FIG. 2 and to compare the average heart rate value to the ranges included in the patient state record to determine a patient state. Referring to FIG. 8, the patient state record 430 includes a first state identifier field 432 and associated heart rate lower and upper bound fields 434 and 436. The first state identifier field 432 stores an identifier that identifies a patient state and the associated heart rate lower and upper bound fields 434 and 436 store lower and upper bounds defining a heart rate value range associated with the state identified by the first state identifier field. The patient state record 430 also includes a second state identifier field 438 and associated heart rate lower and upper bound fields 440 and 442.

In various embodiments, additional or alternative states to those shown in FIG. 8 may be defined in additional or alternative state identifier fields and associated lower and upper heart rate fields included in the patient state record 430.

In various embodiments, the patient state record 430 shown in FIG. 8 may have been previously determined and stored in the location 144 of the storage memory 104. For example, in some embodiments, the patient state record 430 may have been generated and/or updated during training of the forecaster 12, as described in further detail later in this specification.

Block 406 of the flowchart 400 shown in FIG. 6 may direct the forecaster processor 100 shown in FIG. 2 to determine whether the average heart rate value is within the range defined by the heart rate lower and upper bound fields 434 and 436 or within the range defined by the heart rate lower and upper bound fields 440 and 442.

Block 408 may then direct the forecaster processor 100 to, based on the determination made at block 406, determine a patient state. Block 408 may direct the forecaster processor 100 to identify a patient state by identifying the state identifier associated with the range within which the average heart rate fell, as determined at block 406.

For example, in various embodiments, block 406 of the flowchart 400 shown in FIG. 6 may direct the forecaster processor 100 shown in FIG. 2 to determine that the average heart rate value of the identified one or more heart rate records is 83 bpm and block 406 may direct the forecaster processor 100 to determine that the average heart rate value is within the range defined by the fields 434 and 436 of the patient state record 430 shown in FIG. 8. Accordingly, block 408 may direct the forecaster processor 100 to determine that the identifier of "Awake" as stored in the state identifier field 432 identifies the patient state. Block 408 may direct the forecaster processor 100 to store the determined state identifier in the location 146 of the storage memory 104 shown in FIG. 2 as a current patient state identifier.

Each of the patient states identified by the state identifiers may be associated with a set of forecasting parameters. In some embodiments, the forecasting parameters may include blood glucose trend records, which may each include a set of historical blood glucose values and associated time values such that each blood glucose trend record represents blood glucose levels of the patient during a historical time period. The blood glucose trend records may act as forecasting parameters that can be used to forecast or predict a future blood glucose level for the patient, for example, as described below.

The blood glucose trend records may be stored in the location 150 of the storage memory 104 shown in FIG. 2. An exemplary blood glucose trend record 460 is shown in FIG. 9. The blood glucose trend record 460 includes information representing a trend which the blood glucose levels of the patient may be expected to follow. In various embodiments, the blood glucose trend record 460 may represent previously measured blood glucose levels over time for the patient while the patient was in a particular state. Referring to FIG. 9, the blood glucose trend record 460 includes a trend identifier field 461 for storing a unique identifier identifying the blood glucose trend record. The blood glucose trend record 460 also includes a state identifier field 463 for storing an identifier identifying the patient state with which the blood glucose trend record is associated.

The blood glucose trend record 460 shown in FIG. 9 also includes a first blood glucose field 462 for storing a blood glucose value representing a blood glucose level and an associated time field 464 for storing a time value representing a time at which the blood glucose level was sensed. Referring still to FIG. 9, the blood glucose trend record 460 includes further blood glucose fields and associated time fields for storing additional blood glucose values and associated time values. In the embodiment shown in FIG. 9, the blood glucose trend record 460 includes 17 blood glucose fields and associated time fields. However, in various embodiments, blood glucose trend records may include further or fewer blood glucose values for predicting blood glucose values for different various amounts of time in the future.

In some embodiments, a plurality of blood glucose trend records, each having a similar format to the blood glucose trend record 460 shown in FIG. 9, may have been generated and stored in the location 148 of the storage memory 104 during a training period prior to execution of the flowchart 200 shown in FIG. 3, for example, as described further later in this description.

Referring back to FIG. 3, block 208 directs the forecaster processor 100 to apply the set of forecasting parameters associated with the determined patient state to the sensed physiological property indicators to determine at least one forecast physiological property indicator representing a forecast physiological property of the patient at a future time.

In some embodiments, block 208 may direct the forecaster processor 100 to retrieve one or more of the blood glucose trend records stored in the location 148 of the storage memory 104 that are associated with the patient state determined at block 206. Block 208 may direct the forecaster processor 100 to generate a time-dependent function based on at least some of the blood glucose trend records and to determine at least one forecast blood glucose value using the function.

Figure 10:
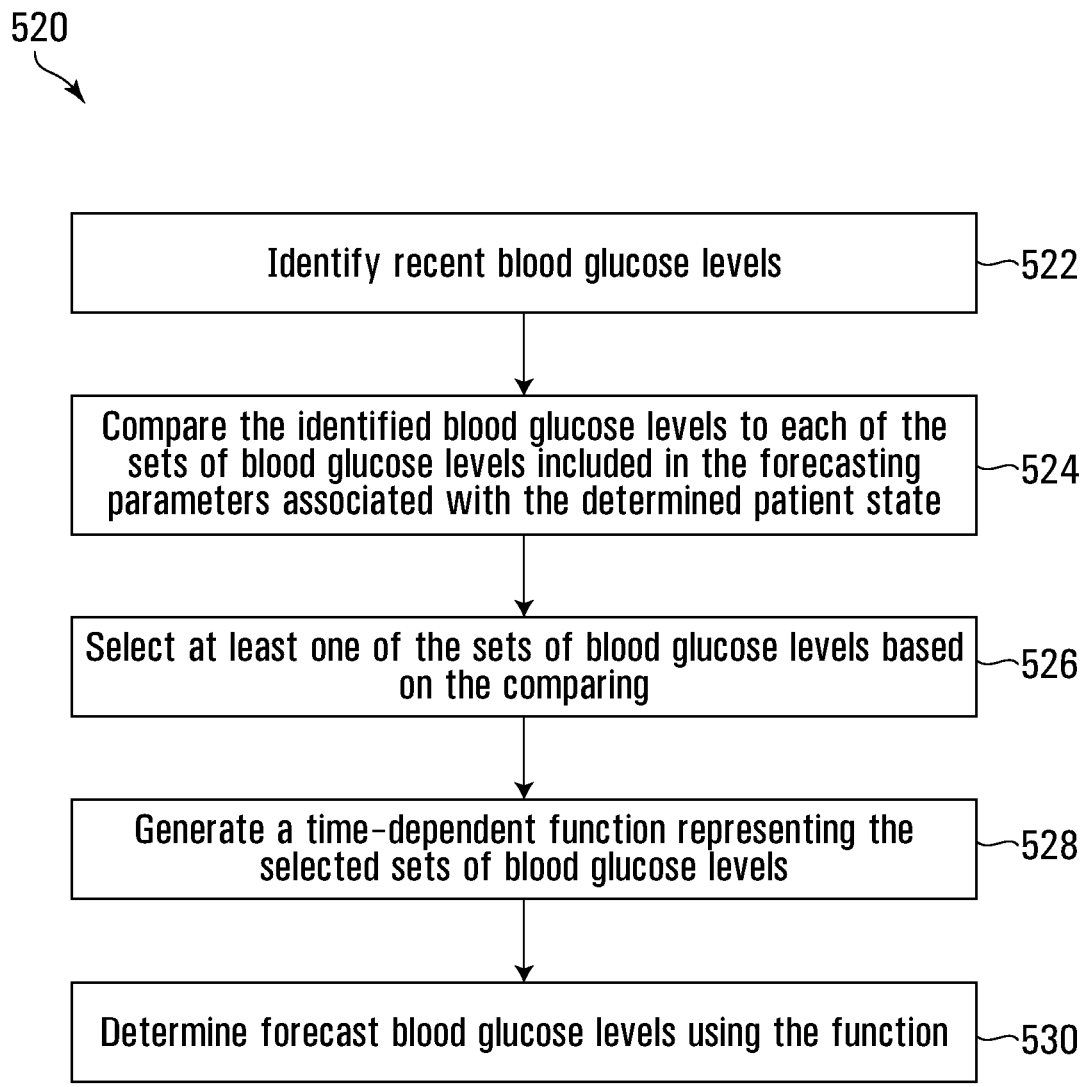
FIG. 10 is a flowchart depicting blocks of code that may be included in the flowchart of FIG. 2 in accordance with various embodiments of the invention.

Referring now to FIG. 10, there is shown a flowchart 520 depicting blocks of code which may be included in the block 208 of the flowchart 200 shown in FIG. 3, in accordance with various embodiments. The blocks of code included in the flowchart 520 may direct the forecaster processor 100 to apply the blood glucose trend records associated with the determined patient state to the sensed blood glucose values to determine at least one forecast blood glucose value representing a forecast blood glucose level of the patient at a future time.

The flowchart 520 shown in FIG. 10 begins with block 522 which directs the forecaster processor 100 shown in FIG. 2 to identify one or more recent blood glucose levels. In various embodiments, block 522 may direct the forecaster processor 100 to identify recent blood glucose values included in blood glucose records stored in the location 140 of the storage memory 104. In some embodiments block 522 may direct the forecaster processor 100 to identify the same blood glucose values previously identified at block 402 of the flowchart 400 shown in FIG. 6 and so block 522 may direct the forecaster processor 100 to read the recently sensed blood glucose record 410 from the location 143 of the storage memory 104.

Block 524 of the flowchart 520 shown in FIG. 10 then directs the forecaster processor 100 to compare the identified blood glucose levels to sets of blood glucose levels included in the forecasting parameters associated with the determined patient state. In various embodiments, block 524 may direct the forecaster processor 100 to compare the blood glucose values of the recently sensed blood glucose record 410 to blood glucose values included in each of the blood glucose trend records stored in the location 144 of the storage memory 104 that are associated with the determined patient state. Block 524 may direct the forecaster processor 100 to determine how well the blood glucose values of the recently sensed blood glucose record 410 fit each of the blood glucose trends represented by the blood glucose trend records. In some embodiments, block 524 may direct the forecaster processor 100 to generate a comparison value for each of the blood glucose trend records, the comparison value representing how well the blood glucose values of the recently sensed blood glucose record 410 fit the blood glucose trend represented by the blood glucose trend record.

Figure 11:
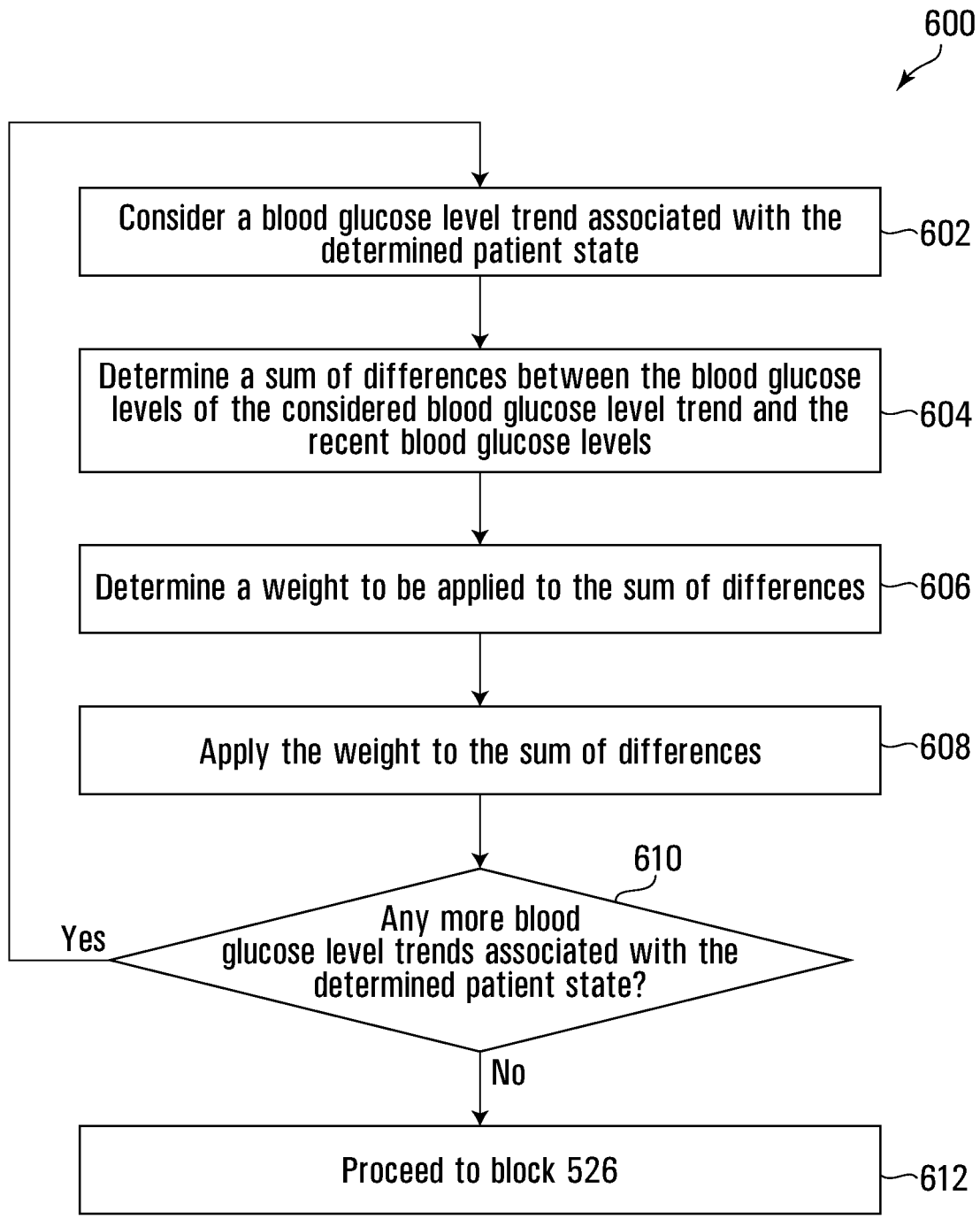
FIG. 11 is a flowchart depicting blocks of code that may be included in the flowchart of FIG. 10 in accordance with various embodiments of the invention.

Referring to FIG. 11, there is provided a flowchart 600 depicting blocks of code that may be included in the block 524 of the flowchart 520 shown in FIG. 10, in accordance with various embodiments. The blocks of code included in the flowchart 600 may direct the forecaster processor 100 to compare the blood glucose values of the recently sensed blood glucose record 410 to sets of blood glucose values represented by the blood glucose trend records.

The flowchart 600 shown in FIG. 11 begins with block 602, which directs the forecaster processor 100 to consider a blood glucose trend associated with the determined patient state. Block 602 may direct the forecaster processor 100 to read the current patient state identifier from the location 146 of the storage memory 104 and to retrieve a blood glucose trend record from the location 148 of the storage memory 104 that includes a state identifier field that matches the current patient state identifier. In some embodiments, for example, the current patient state identifier stored in the location 146 may be "Awake" and block 602 may direct the forecaster processor 100 to retrieve the blood glucose trend record 460 from the location 148 of the storage memory 104.

Block 604 of the flowchart 600 shown in FIG. 11 then directs the forecaster processor 100 shown in FIG. 2 to determine a sum or aggregation of differences between the blood glucose levels of the considered blood glucose trend and the blood glucose values of the recently sensed blood glucose record 410 as generated at block 522 of the flowchart 520 shown in FIG. 10. In various embodiments, a representation of the sum of differences may act as a comparison value that represents how well or poorly the blood glucose values of the recently sensed blood glucose record 410 match the blood glucose values in the blood glucose trend.

In various embodiments, to facilitate forecasting of future blood glucose values using the blood glucose trend records, the time period covered by the blood glucose values of the recently sensed blood glucose record 410 shown in FIG. 7 may be shorter than the time period covered by the blood glucose trend. Thus, block 604 of the flowchart 600 shown in FIG. 11 may direct the forecaster processor 100 shown in FIG. 2 to compare the blood glucose values of the recently sensed blood glucose record 410 to a subset of the blood glucose values included in the blood glucose trend record 460 shown in FIG. 9, the subset representing blood glucose levels over the same length of time as the blood glucose values of the recently sensed blood glucose record 410. In some embodiments, block 604 may direct the forecaster processor 100 to compare the blood glucose values of the recently sensed blood glucose record 410 to blood glucose values in the blood glucose trend record 460 that are associated with the earliest time values in the blood glucose trend record.

For example, in various embodiments, where there are 5 blood glucose values in the recently sensed blood glucose record 410 denoted as $[a_1, a_2, \ldots, a_5]$ and 17 blood glucose values in the blood glucose trend record 460 denoted as $[b_1, b_2, \ldots, b_{17}]$, and both the 5 recent blood glucose values and the first 5 blood glucose values in the blood glucose trend record represent blood glucose levels over the same length of time, block 604 may direct the forecaster processor 100 to determine the sum of differences by determining a Euclidean distance defined as:

$$d = \sqrt{\sum_{i=1}^{5}(a_i - b_i)^2}$$

Block 604 of the flowchart 600 shown in FIG. 11 may direct the forecaster processor 100 shown in FIG. 2 to store the determined distance in the location 150 of the storage memory 104 shown in FIG. 2. In some embodiments, block 604 may direct the forecaster processor 100 to generate a blood glucose trend comparison record 640 shown in FIG. 12 and to set a comparison value field 646 of the blood glucose trend comparison record 640 to store the distance determined at block 604. Block 604 may direct the forecaster processor 100 to store the blood glucose trend comparison record 640 in the location 150 of the storage memory 104.

The blood glucose values of the blood glucose trend record 460 shown in FIG. 9 that are compared to the blood glucose values of the recently sensed blood glucose record 410 shown in FIG. 6 at block 604 may be considered to be fit blood glucose trend values since these values are the ones that are fit or compared to the recently sensed blood glucose values. Blood glucose values included in the blood glucose trend record 460 that are associated with times after the fit blood glucose trend values may be considered to be forecast blood glucose trend values, since these blood glucose values are used for forecasting future blood glucose values, as described in further detail below.

Referring to FIG. 11, in various embodiments, the flowchart 600 may continue at block 606, which directs the forecaster processor 100 shown in FIG. 2 to determine a weight to be applied to the sum of differences determined at block 604. In various embodiments, block 606 may direct the forecaster processor 100 to determine the weight based on an expected probability that the blood glucose trend represented by the blood glucose trend record could occur during a time period associated with the identified recent blood glucose records.

Referring to FIG. 13, there is provided a flowchart 700 depicting blocks of code that may be included in the block 606 of the flowchart 600 shown in FIG. 11, in accordance with various embodiments. The blocks of code included in the flowchart 700 may direct the forecaster processor 100 to determine a weight to be applied to the sum of differences determined at block 604 to provide a weighted comparison value representing how well or poorly the recently sensed blood glucose values fit the considered blood glucose trend.

In various embodiments, the flowchart 700 may direct the forecaster processor 100 to determine a change over time represented by the considered blood glucose trend record and then to determine a representation of a likelihood or probability that the change over time would occur during a time period subsequent to the time at which the most recently sensed blood glucose value was sensed. The flowchart 700 may direct the forecaster processor 100 to determine a weight based on the determined representation of the probability.

The flowchart 700 shown in FIG. 13 begins with block 702 which directs the forecaster processor 100 shown in FIG. 2 to determine a change over time of at least some of the blood glucose values in the considered blood glucose trend record. In various embodiments, block 702 may direct the forecaster processor 100 to determine the change over time of blood glucose values after the fit blood glucose trend values in the blood glucose trend. In some embodiments, as described above where the $1^{st}$ to the $5^{th}$ blood glucose values of the blood glucose trend record were used to determine the sum of differences at block 604, these blood glucose values may act as the fit blood glucose trend values. Subsequent blood glucose values in the record (i.e., the $6^{th}$ blood glucose value to the $17^{th}$ blood glucose value) may act as the forecast blood glucose trend values.

Block 702 may direct the forecaster processor 100 to determine a difference between the value in the $5^{th}$ blood glucose field 466 of the blood glucose trend record 460 shown in FIG. 9 and the value in the final or $17^{th}$ blood glucose value field 476. In various embodiments, where the values stored in the blood glucose value fields 466 and 476 are 158 and 98, block 702 may direct the forecaster processor 100 to determine a change of −60 mg/dL. Block 702 may direct the forecaster processor 100 to determine a change over time or rate of change for the blood glucose values by dividing the difference by the time over which the change occurred. Accordingly, where the time difference between the $5^{th}$ blood glucose value and the $17^{th}$ blood glucose value is 60 minutes or 1 hour, block 702 may direct the forecaster processor 100 to determine the change over time in blood glucose values to be −60 mg/dL per hour.

Block 704 of the flowchart 700 shown in FIG. 13 then directs the forecaster processor 100 shown in FIG. 2 to apply a probability density function to the determined change over time to determine a probability density for the change over time occurring within a time period associated with the recently sensed blood glucose record 410. In some embodiments, a different probability density function may be defined for each 1-hour time period in a day. Each of the probability density functions may be defined by a blood glucose change distribution record and stored in the location 152 of the storage memory 104. In some embodiments, block 704 may direct the forecaster processor 100 to identify a probability density function to be applied by reading a blood glucose change distribution record from the location 152 of the storage memory 104.

An exemplary blood glucose change distribution record 740 is shown in FIG. 14. Referring to FIG. 14, the blood glucose change distribution record 740 includes a first time period field 744 and associated mean and standard deviation fields 746 and 748. The first time period field 744 stores an identifier representing a time period for which a Gaussian function defined by values stored in the associated mean and standard deviation fields 746 and 748 provides a probability density that may be used to determine a weight. In some embodiments, the Gaussian function defined by the values stored in the mean and standard deviation fields 746 and 748 may take as an input a change over time or rate of change in blood glucose values and return a value between 0 and 1 that represents a probability density for the input change over time occurring during the time period identified by the identifier stored in the first time period field 744.

The blood glucose change distribution record 740 may include a plurality of time period fields for storing identifiers that identify respective time periods in a day, for example. In one embodiment, the first time period field 744 may store a value of 0, which may represent a time period of between 12:00 midnight and 1:00 am in any day. A second time period field 750 may store a value of 1 which may represent a time period of between 1:00 am and 2:00 am in a day. Each hour-long portion of the day may be represented by a respective time period field stored in the blood glucose change distribution record 740.

In some embodiments different recurring time periods may be used. For example, in some embodiments, the blood glucose change distribution record 740 may include time period fields that identify time periods on specific days of the week. In such embodiments, for example, a time period of 12:00 pm to 1:00 pm on a Saturday or Sunday may be identified using a different identifier (and therefore different associated mean and variance values) from a time period of 12:00 pm to 1:00 pm on a Monday to Friday. In various embodiments, this may facilitate more accurate forecasting of future blood glucose values, especially when certain days can be associated with different changes in blood glucose throughout the day.

Referring to FIG. 13, in some embodiments, block 704 may direct the forecaster processor 100 shown in FIG. 2 to identify a time period field in the blood glucose change distribution record 740 shown in FIG. 14 that includes a time period identifier that corresponds to the recently sensed blood glucose record 410 shown in FIG. 7 and to use the associated mean and variance values to generate and apply a Gaussian function to the change over time determined at block 702. In some embodiments, block 704 may direct the forecaster processor 100 to look for a time period identifier in the blood glucose change distribution record 740 that identifies a time period that includes the most recent time in the recently sensed blood glucose record 410 and determine that this time period identifier corresponds to the recently sensed blood glucose record 410. Accordingly, in various embodiments where the most recent time value in the recently sensed blood glucose record 410 represents a time of 12:25 pm, block 704 may direct the forecaster processor 100 to identify the 12th time period field 760, storing an identifier set to 12 and representing a time period of between 12:00 pm and 1:00 pm, as corresponding to the recently sensed blood glucose record 410.

In response to this determination, block 704 of the flowchart 700 shown in FIG. 13 may direct the forecaster processor 100 shown in FIG. 2 to use a Gaussian function with the previously determined change over time of blood glucose values as the input, to determine a probability density for the blood glucose trend record 460 occurring during the time period using the following equation:

$$p(x) = \frac{1}{\sqrt{2\pi\sigma^2}} e^{\frac{-(x-\mu)^2}{2\sigma^2}}$$

where x is the change over time previously determined, $\mu$ is the mean value taken from the mean field associated with the identified time period field, and $\sigma$ is the variance value taken from the variance field associated with the identified time period field.

For example, in various embodiments, where the change over time was previously determined to be −60 mg/dL per hour, block 704 may direct the forecaster processor 100 to use the value of −10 stored in the mean field 762 and the value of 30 stored in the variance field 764 of the blood glucose change distribution record 740 to determine the probability density as 0.00331590.

Referring to FIG. 13, block 706 then directs the forecaster processor 100 shown in FIG. 2 to determine a weight based on the determined probability density. For example, in some embodiments, block 706 may direct the forecaster processor 100 to determine the weight to be the inverse of the determined probability density. Accordingly, in various embodiments, as probability density decreases, weight increases, and the distance previously determined is magnified in the comparison value.

After block 706 of the flowchart 700 shown in FIG. 13 has been executed, referring back to FIG. 11, block 606 may be completed. Block 608 then directs the forecaster processor 100 shown in FIG. 2 to apply the weight to the sum of differences. In various embodiments, block 608 may direct the forecaster processor 100 to read the blood glucose trend comparison record 640 from the location 150 of the storage memory 104 and to apply the weight to the value stored in the comparison value field 646. Block 608 may direct the forecaster processor 100 to multiply the value stored in the comparison value field 646 by the determined weight and to store the result in the comparison value field 646. The blood glucose trend comparison record 640 is shown in FIG. 15 after having been updated at block 608. In various embodiments, a high comparison value may indicate that the recently sensed blood glucose record 410 does not fit well with the considered blood glucose trend record, whereas a low comparison value may indicate that the recently sensed blood glucose record 410 fits well with the considered blood glucose trend record.

Referring to FIG. 11, block 610 then directs the forecaster processor 100 shown in FIG. 2 to determine whether there are any more blood glucose trend records associated with the determined patient state. Block 610 may direct the forecaster processor 100 to determine whether any blood glucose trend records stored in the location 148 of the storage memory 104 have not yet been considered at blocks 602 to 608 and include a state identifier that corresponds to the current patient state identifier stored in the location 146 of the storage memory 104. If at block 610 the forecaster processor 100 determines that a further blood glucose trend record has not been considered and includes a state identifier that corresponds to the current patient state identifier, the forecaster processor 100 returns to block 602 and considers the further blood glucose trend record. Otherwise, block 610 directs the forecaster processor 100 to proceed to block 612.

Accordingly, blocks 602 to 608 of the flowchart 600 shown in FIG. 11 may be executed by the forecaster processor 100 shown in FIG. 2 for each of the blood glucose trend records stored in the location 148 of the storage memory 104 that are associated with the current patient state. Thus, when the forecaster processor 100 is directed to proceed to block 612, there may be stored in the location 150 of the storage memory 104 a plurality of blood glucose trend comparison records, each having format generally similar to the blood glucose trend comparison record 640 shown in FIG. 15.

Block 612 directs the forecaster processor 100 to proceed to block 526 of the flowchart 520 shown in FIG. 10. Referring to FIG. 10, block 526 directs the forecaster processor 100 to select at least one of the sets of blood glucose levels based on the comparing performed at block 524. In some embodiments, block 526 may direct the forecaster processor 100 to select at least one of the blood glucose trend records stored in the location 148 of the storage memory 104 based on the associated comparison values stored in the location 150 of the storage memory 104. For example, in some embodiments, block 526 may direct the forecaster processor 100 to select blood glucose trend records that are associated with the lowest comparison values. The selected blood glucose trend records may represent blood glucose trends that best fit the recently sensed blood glucose record 410.

The number of blood glucose trend records selected may be chosen such that a weighted average of changes represented by the selected blood glucose trend records can be used as a function to forecast future blood glucose levels. In some embodiments, for example, block 526 may direct the forecaster processor 100 to select the 50 blood glucose trend records that are associated with the lowest comparison values.

Block 528 of the flowchart 520 shown in FIG. 10 then directs the forecaster processor 100 shown in FIG. 2 to generate a time-dependent function representing the selected sets of blood glucose levels. In some embodiments, block 528 may direct the forecaster processor 100 to generate a function that maps future times to forecast changes or differences in blood glucose levels.

Block 528 may direct the forecaster processor 100 to generate and store a forecast blood glucose change record 800 as shown in FIG. 16 in the location 154 of the storage memory 104, the forecast blood glucose change record defining the function. Referring to FIG. 16, the forecast blood glucose change record 800 includes a plurality of blood glucose change fields, each associated with a time change field. Each of the blood glucose change fields stores a value representing an expected change in blood glucose value over an associated time. In various embodiments, by applying the forecast blood glucose change record to a starting blood glucose value and time, one may be able to forecast future blood glucose values at various future times.

In some embodiments, the number of blood glucose change fields included in the forecast blood glucose change record 800 shown in FIG. 16 may be set to the minimum number of forecast blood glucose trend values included in a blood glucose trend record value. In the embodiment shown in FIG. 16 there are 12 blood glucose change fields included in the forecast blood glucose change record 800, representing forecast blood glucose changes for up to 60 minutes in the future.

In various embodiments, block 528 may direct the forecaster processor 100 to set the values of the blood glucose change fields and associated time fields of the forecast blood glucose change record 800 shown in FIG. 16 by averaging changes in blood glucose values over time, as represented by the selected blood glucose trend records. Block 528 may direct the forecaster processor 100 to average changes in blood glucose values for the blood glucose values in the blood glucose trend records that are after the fit blood glucose values (i.e. changes represented by the $6^{th}$ to $17^{th}$ blood glucose values in the blood glucose trend record 460 shown in FIG. 9). Block 528 may direct the forecaster processor 100 to, for each blood glucose trend record, determine changes at respective times by subtracting the $5^{th}$ blood glucose value and time from each of the blood glucose values and associated times included in the blood glucose trend records.

In some embodiments, block 528 may direct the forecaster processor 100 to average the changes using a weighted average of the changes represented by the selected blood glucose trend records, the weighted average being weighted using the comparison values associated with each blood glucose trend record.

For example, in various embodiments, where 50 blood glucose trend records are selected at block 526 of the flowchart 520 shown in FIG. 10, block 528 may direct the forecaster processor 100 to determine a value for the first blood glucose change field 802 shown in FIG. 16 using the following equation:

$$BG_{change} = \frac{\sum_{i=1}^{50} \frac{\Delta t_i}{c_i}}{\sum_{i=1}^{50} \frac{1}{c_i}}$$

where $\Delta t_i$ is the difference between the $6^{th}$ blood glucose value and the $5^{th}$ blood glucose value for the $i^{th}$ one of the selected blood glucose trend records and where $c_i$ is the comparison value taken from the blood glucose trend comparison record associated with the $i^{th}$ one of the selected blood glucose trend records.

Block 528 may direct the forecaster processor 100 to determine values for the second and subsequent blood glucose change fields in the forecast blood glucose change record 800 generally as described above for the first blood glucose change field 862, but using the $7^{th}$ and subsequent blood glucose values instead of the $6^{th}$ blood glucose value to determine $\Delta t_i$.

Accordingly, block 528 may direct the forecaster processor 100 to determine values for the first blood glucose change fields of the forecast blood glucose change record 800 using the following equation:

$$BG_{change}^j = \frac{\sum_{i=1}^{50} \frac{\Delta t_i^j}{c_i}}{\sum_{i=1}^{50} \frac{1}{c_i}}$$

Where j is used to index which blood glucose change field is being determined. Where $\Delta t_i^j$ is the difference between the (j+5)-th blood-glucose value and the 5th blood-glucose value for the i-th one of the selected blood-glucose trend records and where $c_i$ is the comparison value taken from the blood-glucose trend comparison record associated with the i-th one of the selected blood-glucose trend records.

Referring to FIG. 10, block 530 then directs the forecaster processor 100 shown in FIG. 2 to determine the at least one forecast patient physiological property level using the function determined at block 528. Block 530 may direct the forecaster processor 100 to apply the function defined by the forecast blood glucose change record 800 shown in FIG. 16 to the most recent of the blood glucose values included in the recently sensed blood glucose record 410 shown in FIG. 7.

For example, in some embodiments, block 530 of the flowchart 520 shown in FIG. 10 may direct the forecaster processor 100 shown in FIG. 2 to generate values for blood glucose fields and associated time fields of a forecast blood glucose record 860 shown in FIG. 17 by adding the most recent blood glucose value and associated time value from the recently sensed blood glucose record 410 to each of the blood glucose change and time fields in the forecast blood glucose change record 800. Block 530 may direct the forecaster processor 100 to store the forecast blood glucose record 860 in the location 154 of the storage memory 104. In various embodiments, each of the blood glucose value fields included in the forecast blood glucose record 860 may store a forecast blood glucose value associated with a future time represented by a time value stored in an associated time field.

Referring back to FIG. 3, in some embodiments, block 208 of the flowchart 200 may direct the forecaster processor 100 shown in FIG. 2 to produce signals for causing at least one display to display a representation of the forecast physiological properties. For example, in some embodiments, block 208 may direct the forecaster processor 100 to produce signals representing the forecast blood glucose record 860 shown in FIG. 17 for causing a representation of the forecast blood glucose record 860 to be transmitted to the patient device 20 shown in FIG. 1 via the interface 124 of the I/O interface 112 of the forecaster 12 and the network 18. The patient device 20 may be configured to receive the data included in the forecast blood glucose record 860 and to produce signals for causing a display of the patient device to display a representation of the received information. For example, a display that may be provided by the display of the patient device 20 is shown at 900 in FIG. 18. The display 900 includes a representation 902 of the blood glucose values included in the forecast blood glucose record 860.

Figure 18:
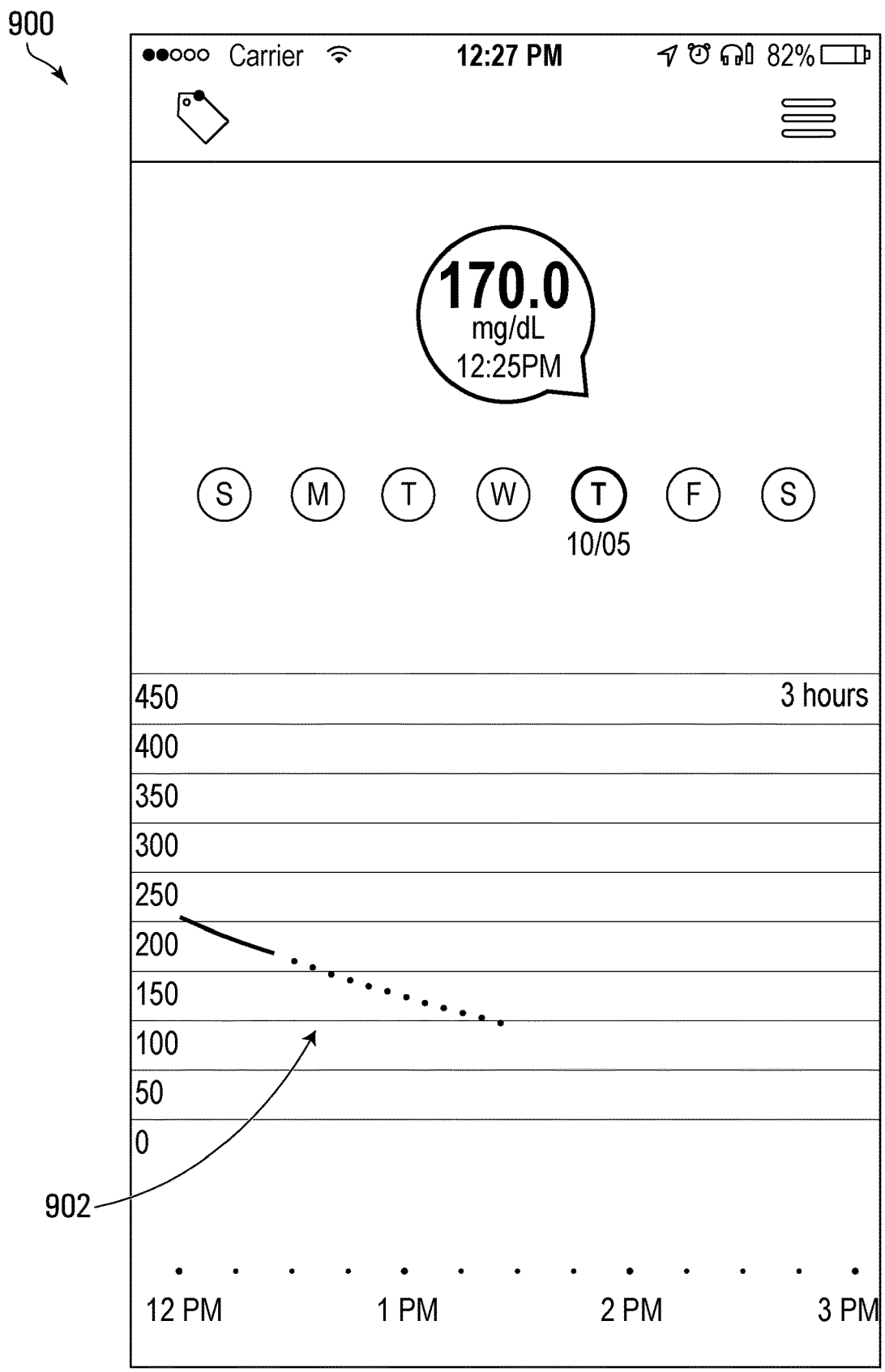
FIG. 18 is a representation of an exemplary display of a patient device included in the system shown in FIG. 1 in accordance with embodiments of the invention.

A patient regulating insulin or a computer directed by a software algorithm for managing insulin injection, upon reviewing the representation 902 shown in FIG. 18 of the forecast future blood glucose values representing forecast future blood glucose levels of the patient, may consider whether the forecast future blood glucose levels are desirable and/or acceptable. If it is determined that the forecast future blood glucose levels are undesirable or unacceptable, the patient or the computer may take steps to correct blood glucose levels in response to the patient's forecasted glucose to avoid the forecast future blood glucose levels becoming a reality.

Blood Glucose Trend Training

Figure 19:
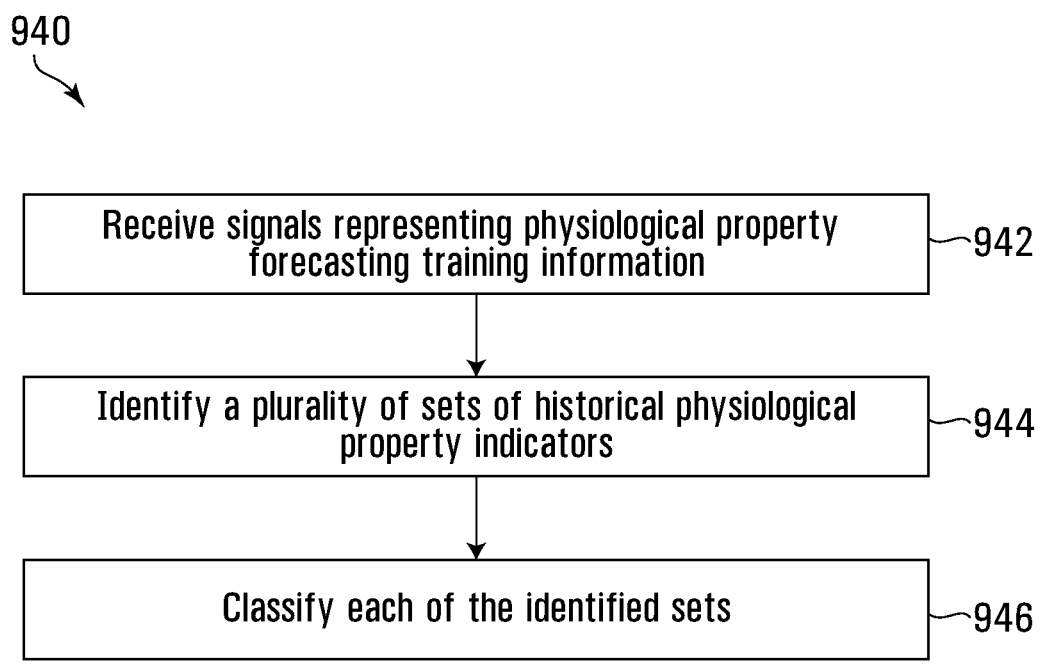
FIG. 19 is a flowchart depicting blocks of code for directing the forecaster of the system of FIG. 1 to perform training functions in accordance with various embodiments of the invention.

As described above, the blood glucose trend records stored in the location 148 of the storage memory 104 shown in FIG. 2 may be previously collected and stored during a training phase. Referring now to FIG. 19, a flowchart depicting blocks of code for directing the forecaster processor 100 shown in FIG. 2 to perform training functions in accordance with one embodiment is shown generally at 940. The blocks of code included in the flowchart 940 may be encoded in the block of codes 162 of the program memory 102 shown in FIG. 2, for example.

In some embodiments, the flowchart 940 shown in FIG. 19 may be executed during a training phase which may occur prior to and/or contemporaneously with the forecasting process described with reference to the flowchart 200 shown in FIG. 3. In various embodiments, execution of the flowchart 940 may cause the forecaster processor 100 to generate and store blood glucose trend records in the location 148 of the storage memory 104.

The flowchart 940 shown in FIG. 19 begins with block 942 which directs the forecaster processor 100 shown in FIG. 2 to receive signals representing physiological property forecasting training information, the training information including historical physiological property indicators and contextual indicators, each contextual indicator associated with at least one of the historical physiological property indicators. In various embodiments, the historical physiological property indicators may include blood glucose values and the contextual indicators may include heart rate values and block 942 may include blocks of code that are generally similar to the blocks 202 and 204 of the flowchart 200 shown in FIG. 3 and described above.

Accordingly, block 942 may direct the forecaster processor 100 to store blood glucose records in the location 140 of the storage memory 104 and to store heart rate records in the location 142 of the storage memory 104. In some embodiments, many blood glucose records and heart rate records may need to be received and stored at block 942 to facilitate accurate forecasting after training. For example, in some embodiments, blood glucose records and heart rate records representing blood glucose levels and heart rates sensed at 5-minute intervals over a specific time period, such as, for example, between 14 and 28 days, may need to be stored in the location 140 of the storage memory 104 and considered at blocks 944 and 946 of the flowchart 940 before training can be considered adequate.

Block 944 of the flowchart 940 shown in FIG. 19 directs the forecaster processor 100 shown in FIG. 2 to identify a plurality of sets of historical physiological property indicators from the historical physiological property indicators. Block 944 may direct the forecaster processor 100 to look for trends in the blood glucose values over time and for each trend that is found, to identify the blood glucose values in the trend as a set of blood glucose values. In various embodiments, identifying a set of blood glucose values may involve generating a blood glucose trend record including the identified set of blood glucose values and associated time values and storing the blood glucose trend record in the location 148 of the storage memory 104.

Figure 20:
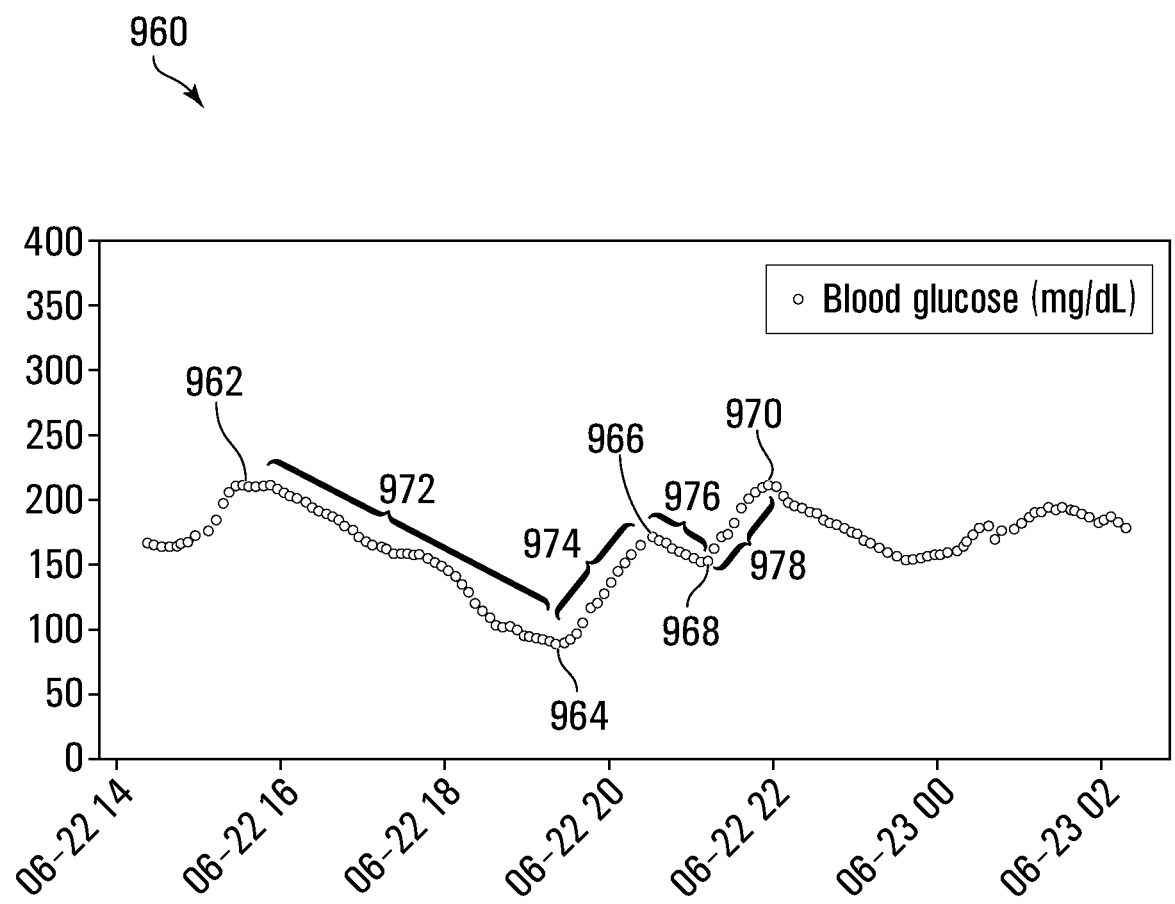
FIG. 20 is a representation of a graph depicting some exemplary blood glucose levels represented by blood glucose records stored by the forecaster of the system shown in FIG. 1, in accordance with various embodiments of the invention.

In some embodiments, a trend may include blood glucose values that are associated with related time values and represent a continuous or generally continuous increase or decrease in blood glucose levels. In some embodiments, block 944 may direct the forecaster processor 100 to find a trend by identifying consecutive corrections in blood glucose values and determining that the trend includes the blood glucose values that are associated with times between those corrections. Corrections may correspond to a change in sign of the slope of blood glucose levels over time, which may occur as a result of insulin injection, activity, or carbohydrate ingestion, for example. Referring to FIG. 20, there is shown a graph 960 depicting some exemplary blood glucose levels represented by blood glucose records stored in the location 140 of the storage memory 104, in accordance with one embodiment.

In various embodiments, block 944 of the flowchart 940 shown in FIG. 19 may direct the forecaster processor 100 shown in FIG. 2 to identify respective sets of blood glucose values 972, 974, 976, and 978 between corrections 962, 964, 966, 968, and 970. Block 944 may direct the forecaster processor 100 to store one or more representation of each of the identified sets of blood glucose values 972, 974, 976, and 978 as a respective blood glucose trend record having format generally similar to the blood glucose trend record 460 shown in FIG. 8. Referring to FIG. 21, there is shown an exemplary blood glucose trend record 1000, which may be generated at block 944, representing a portion of the set of blood glucose values 972 shown in FIG. 20. In various embodiments, block 944 may direct the forecaster processor 100 to initialize the state identifier field 1002 of the blood glucose trend record 1000 to a NULL value, which may then be set at block 946.

In some embodiments, block 944 of the flowchart 940 shown in FIG. 19 may direct the forecaster processor 100 shown in FIG. 2 to apply one or more filters to each of the identified sets of blood glucose values before generating and storing a blood glucose trend record representing the set. For example, in some embodiments, block 944 may direct the forecaster processor 100 to filter out or disregard any set of blood glucose values that does not begin with at least a threshold number of consecutive, evenly spaced in time, blood glucose values. For example, in some embodiments, block 944 may direct the forecaster processor 100 to disregard any set of blood glucose values that does not begin with 17 consecutive, evenly spaced in time (and therefore not missing any blood glucose values), blood glucose values.

In some embodiments, block 944 may direct the forecaster processor 100 to split each identified set of blood glucose values into respective sets of 17 blood glucose values and associated times and to generate respective blood glucose trend records representing each set of 17 blood glucose values and associated times. In some embodiments, for example, blood glucose trend records may include fewer or additional blood glucose values.

Referring to FIG. 19, block 946 directs the forecaster processor 100 shown in FIG. 2 to classify each of the sets of historical physiological property indicators based on the contextual indicators associated with the physiological indicators included in the sets. In some embodiments, block 946 may direct the forecaster processor 100 to classify each of the blood glucose trend records generated at block 944 and stored in the location 148 of the storage memory 104 based on heart rates represented by the heart rate records stored in the location 142 of the storage memory 104.

For example, in some embodiments, block 946 of the flowchart 940 shown in FIG. 19 may direct the forecaster processor 100 shown in FIG. 2 to, for each of the blood glucose trend records generated at block 944, identify one or more heart rate values associated with the blood glucose values included in the blood glucose trend record and determine whether the one or more heart rate values are within one of a plurality of heart rate ranges. Block 946 may include code generally similar to the code described above having regard to blocks 404 and 406 of the flowchart 400 shown in FIG. 6, but considering blood glucose values in a blood glucose trend record. Block 946 may then direct the forecaster processor 100 to determine a patient state to be associated with the blood glucose trend record based on a determined average heart rate, generally as described above having regard to block 408 of the flowchart 400 shown in FIG. 6.

Block 946 may direct the forecaster processor 100 to, for each of the generated blood glucose trend records, set the state identifier field of the blood glucose trend record according to the determined patient state for that blood glucose trend record. For example, in some embodiments, block 946 may direct the forecaster processor 100 to determine an average heart rate value of 90 bpm for heart rate values associated with the blood glucose trend record 1000 generated at block 944 and to set the state identifier field 1002 of the blood glucose trend record 1000 accordingly, as shown in FIG. 22.

Patient State Training

As described above, in some embodiments, the contents of the patient state record 430 shown in FIG. 8 and stored in the location 144 of the storage memory 104 shown in FIG. 2 may have been previously determined during a training phase. For example, in some embodiments, the block of codes 162 of the program memory 102 shown in FIG. 2 may include patient state training blocks of code for directing the forecaster processor 100 to perform patient state training functions. These blocks of code may be executed during a training phase which may occur prior to and/or contemporaneously with forecasting as described with reference to the flowchart 200 shown in FIG. 3. In various embodiments, the patient state training blocks of code may direct the forecaster processor 100 to generate or update the patient state record 430 shown in FIG. 8 and stored in the location 144 of the storage memory 104 shown in FIG. 2.

Figure 23:
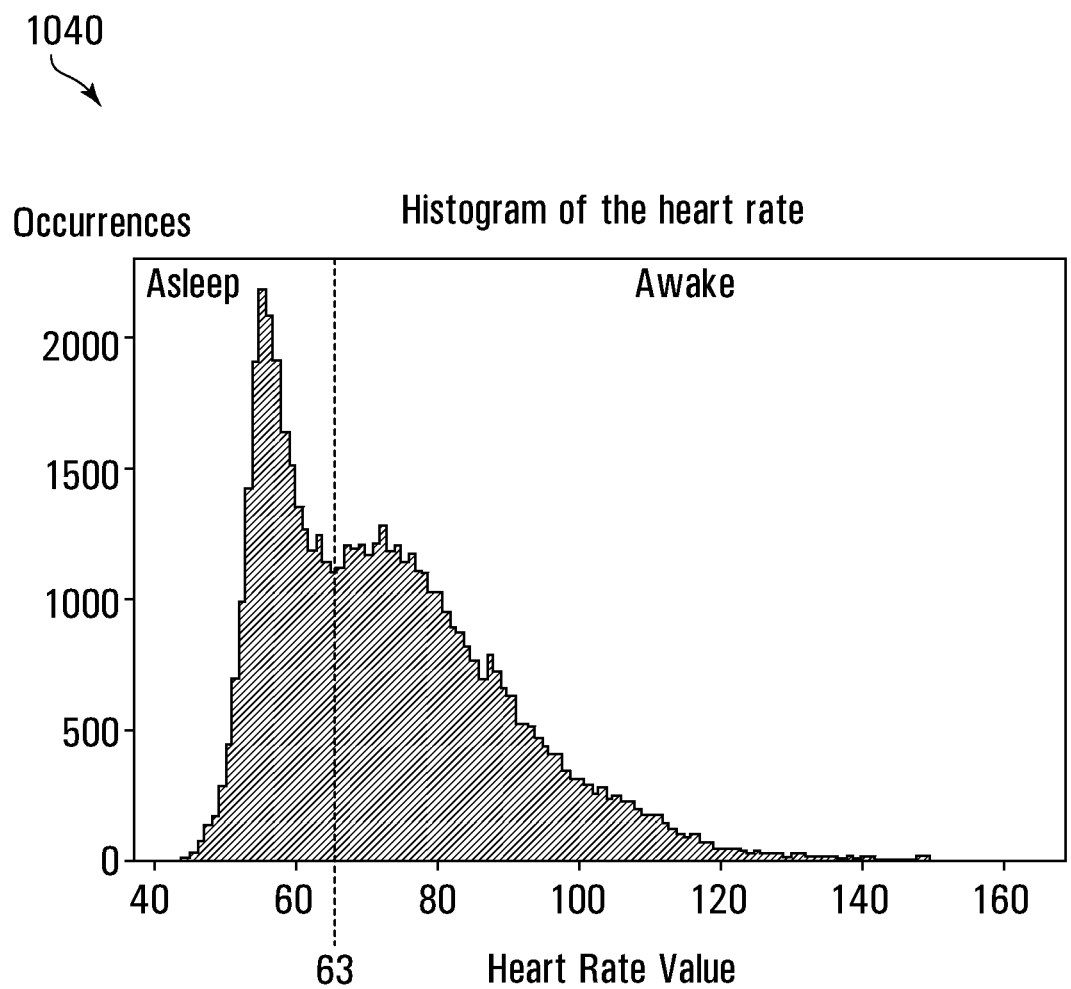
FIG. 23 is a representation of a histogram depicting exemplary heart rates represented by heart rate records stored by the forecaster of the system shown in FIG. 1, in accordance with various embodiments of the invention.

The patient state training block of codes may direct the forecaster processor 100 to receive heart rate values and associated time values and to generate and store heart rate records, generally as described having regard to block 204 of the flowchart 200. Referring to FIG. 23, there is shown at 1040 a histogram of heart rates represented by the heart rate records stored in the location 142 of the storage memory 104, in accordance with one embodiment.

The patient state training block of codes may direct the forecaster processor 100 to identify clusters of heart rate values from the heart rate values represented by the heart rate records. For example, in some embodiments, the patient state training block of codes may direct the forecaster processor 100 to identify two gaussian clusters of heart rate values from the heart rate records. The patient state training block of codes may direct the forecaster processor 100 to determine a boundary heart rate from the identified gaussian clusters. For example, in some embodiments, the patient state training block of codes may direct the forecaster processor 100 to determine a boundary heart rate value as a middle heart rate value between the mean heart rates of adjacent identified gaussians. The patient state block of codes may direct the forecaster processor 100 to set heart rate lower and upper bound fields included in the patient state record 430 shown in FIG. 8 based on the determined boundary heart rate values.

For example, in some embodiments, the patient state block of codes may direct the forecaster processor 100 to set the heart rate lower bound field 434 of the patient state record 430 shown in FIG. 8 associated with the "Awake" state to the boundary heart rate value and to set the heart rate upper bound field 442 associated with the "Asleep" state to the boundary heart rate value, based on the heart rate records represented by the histogram 1040 shown in FIG. 23.

In some embodiments, the patient state block of codes may direct the forecaster processor 100 to set the heart rate lower bound field 440 associated with the "Asleep" state to a value of 0 and to set the heart rate upper bound field 436 associated with the "Awake" state to a default value of 999. In some embodiments, the heart rate lower bound field 440 and heart rate upper bound field 426 of the patient state record 430 shown in FIG. 8 may be omitted.

In various embodiments, the patient state block of codes may direct the forecaster processor 100 to identify additional clusters of heart rates associated with additional states. For example, in some embodiments the block of codes may direct the forecaster processor 100 to identify an "Awake" state, an "Active-moving or walking around" state, a "sports" state, and/or a "Stress" state with elevated heart rate and low activity.

Blood Glucose Change Training

As described above, in some embodiments, the contents of the blood glucose change distribution record 740 shown in FIG. 14 and stored in the location 152 of the storage memory 104 shown in FIG. 2 may have been previously determined during a training phase. For example, in some embodiments, the block of codes 162 of the program memory 102 may include blood glucose change training code for directing the forecaster processor 100 to perform blood glucose change training functions and to generate or update the blood glucose change distribution record 740 shown in FIG. 14. This code may be executed during a training phase which may occur prior to and/or contemporaneously with forecasting as described with reference to the flowchart 200 shown in FIG. 3.

In various embodiments, the blood glucose change training code included in the block of codes 162 may direct the forecaster processor 100 to determine, for each time period included in the blood glucose change distribution record 740, mean and variance values defining a gaussian function for providing a probability density based on a given change in blood glucose values over time. In some embodiments, the blood glucose change training code may direct the forecaster processor 100 to determine the mean and variance values for a given time period based on historical changes in blood glucose values during that time period.

Figure 24:
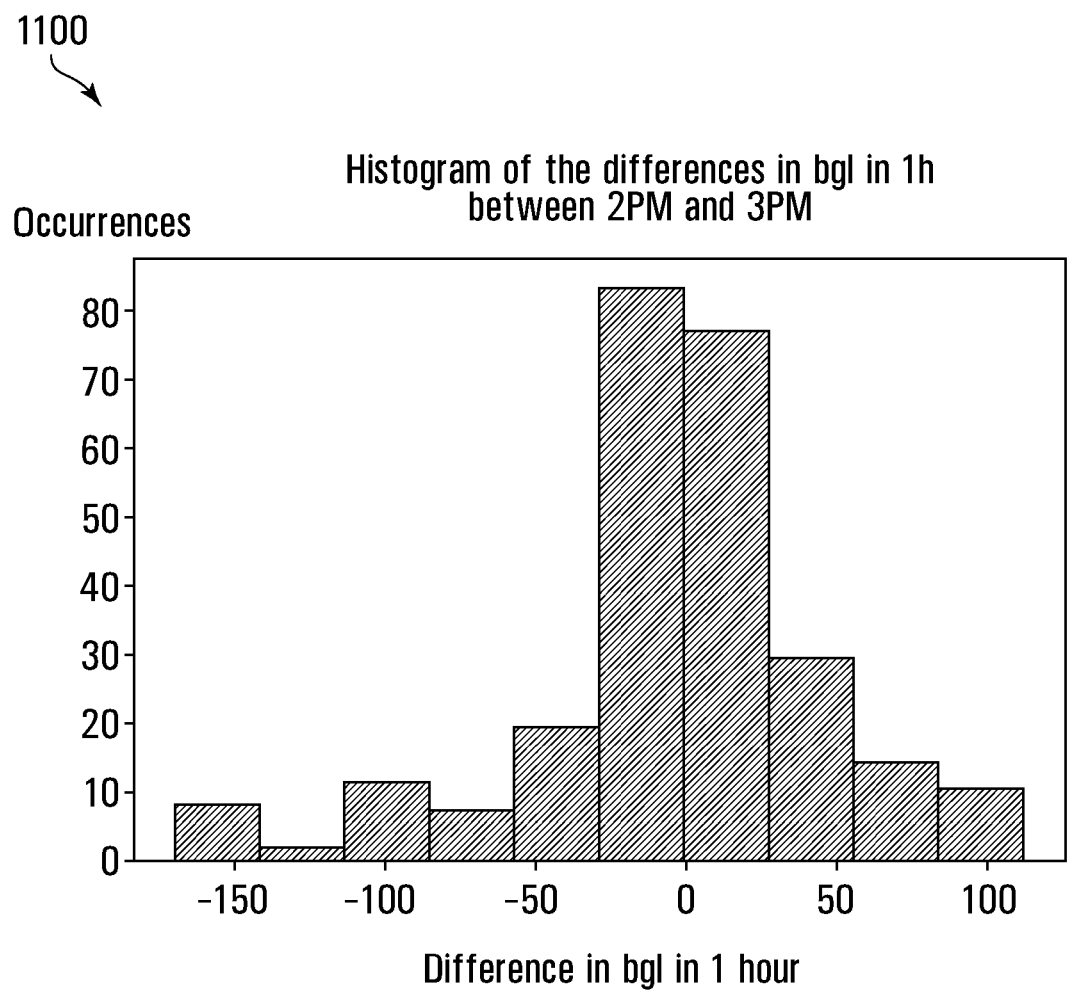
FIG. 24 is a representation of a histogram depicting differences or changes in blood glucose levels represented blood glucose records stored by the forecaster of the system shown in FIG. 1, in accordance with various embodiments of the invention.

For example, in some embodiments, the blood glucose change training code may direct the forecaster processor 100 to read the blood glucose records stored in the location 140 of the storage memory and determine, for each time period, what historical changes in blood glucose levels occurred during the time period. Referring to FIG. 24, there is shown a histogram 1100 representing the differences or change in blood glucose levels in the one-hour time period between 2:00 pm and 3:00 pm as determined by analyzing the blood glucose records stored in the location 140 of the storage memory 104, in accordance with one embodiment.

The blood glucose change training code may direct the forecaster processor 100 to fit a gaussian function to the histogram 1100 shown in FIG. 24 by determining the mean and variance from the change values represented by the histogram. The blood glucose change training code may direct the forecaster processor 100 to set the mean and variance fields of the blood glucose change distribution record 740, which are associated with the time period field having a value of 14 to the determined mean and variance for the histogram 1100 shown in FIG. 24. In various embodiments, a mean and variance for each of the time periods represented by the blood glucose change distribution record 740 shown in FIG. 14 may be set generally similar.

Probability Density Function

In various embodiments, the probability density function used at block 704 of the flowchart 700 shown in FIG. 13 may be a function or map that is different from the Gaussian function described above. For example, in some embodiments, the probability density function used at block 704 of the flowchart 700 shown in FIG. 13 may include one or more maps from blood glucose changes over time to values representing probability density, each of the maps associated with a particular time period. In some embodiments, the maps may have been previously determined and respective blood glucose change distribution records representing each of the maps may be stored in the location 152 of the storage memory 104.

Referring to FIG. 25, there is shown an exemplary blood glucose change distribution record 1400 that may be stored in the location 152 of the storage memory 104, in accordance with some embodiments, and which represents a map from changes over time in blood glucose to probability densities.

The blood glucose change distribution record 1400 shown in FIG. 25 represents a density histogram that spans from −390 mg/dL per hour to +390 mg/dL per hour by steps of 30 mg/dL per hour and is associated with a time period of between 12:00 pm to 1:00 pm. The blood glucose change distribution record 1400 shown in FIG. 25 is exemplary. In various embodiments, a blood glucose change distribution record generally similar to the blood glucose change distribution record 1400 may be used which represents a density histogram that has a different breadth and/or step size, for example.

Referring to FIG. 25, the blood glucose change distribution record 1400 includes a time period identifier field 1402 for storing an identifier identifying a time period with which the record 1400 is associated. The blood glucose change distribution record 1400 also includes pairs of associated blood glucose change range fields and probability density fields, each blood glucose change range field storing a value representing a range of blood glucose changes and each associated probability density field storing a value representing a probability density or likelihood that a blood glucose change that is within the range represented by the blood glucose change range field would take place during the time represented by the value stored in the time period identifier field 1402. The blood glucose change distribution record 1400 includes blood glucose change fields spanning from −390 mg/dL per hour to +390 mg/dL per hour by steps of 30 mg/dL per hour.

Multiple blood glucose change distribution records having a format generally similar to that of the blood glucose change distribution record 1400 shown in FIG. 25 may be stored in the location 152 of the storage memory 104, each associated with a respective time period.

In some embodiments, block 704 of the flowchart 700 shown in FIG. 13 may direct the forecaster processor 100 to identify a blood glucose change distribution record stored in the location 152 of the storage memory 104 that includes a time period identifier that corresponds to the recently sensed blood glucose record 410 shown in FIG. 7 and to use the identified blood glucose change distribution record to map the change over time determined at block 702 to a value representing probability density.

In various embodiments where the most recent time value in the recently sensed blood glucose record 410 represents a time of 12:25 pm, block 704 may direct the forecaster processor 100 to identify the blood glucose change distribution record 1400 shown in FIG. 25 that includes an identifier set to 12 and represents a time period of between 12:00 pm and 1:00 pm, as corresponding to the recently sensed blood glucose record 410. In response to this determination, block 704 of the flowchart 700 shown in FIG. 13 may direct the forecaster processor 100 shown in FIG. 2 to compare the previously determined change over time of blood glucose values with the blood glucose change range fields of the blood glucose change distribution record 1400 to determine an associated probability density for the considered blood glucose trend record.

Block 706 of the flowchart 700 shown in FIG. 13 may then direct the forecaster processor 100 to determine a weight based on the determined probability density, generally as described above.

In some embodiments, before block 706 is executed, block 704 may direct the forecaster processor 100 to apply a correction to the probability density determined at block 706. For example, in some embodiments, block 704 may direct the forecaster processor 100 to determine a probability density correction value using a probability density correction record 1460 shown in FIG. 26 and to apply the probability density correction value to the probability density determined at block 704. In various embodiments, the probability density correction value may facilitate considering that the blood glucose trend records already reflect a general probability of observing a specific blood glucose change over time (the more likely a change over time is to appear, the more it will be present in our library and the more likely it will be selected).

In some embodiments, the probability density correction record 1460 may have been previously generated and stored in the location 152 of the storage memory 104, during a training period for example. The probability density correction record 1460 shown in FIG. 26 includes pairs of associated blood glucose change range fields and probability density correction fields. Block 704 may direct the forecaster processor 100 to compare the previously determined change over time of blood glucose values with the blood glucose change range fields to determine an associated probability density correction and to divide the probability density previously determined by the probability density correction to determine a corrected probability density. The corrected probability density may be treated as the probability density generally as described above.

In some embodiments, the contents of the blood glucose change distribution record 1400 and/or the probability density correction record 1460 shown in FIGS. 25 and 26 and stored in the location 152 of the storage memory 104 shown in FIG. 2 may have been previously determined during a training phase. For example, in some embodiments, the block of codes 162 of the program memory 102 may include blood glucose change training code for directing the forecaster processor 100 to perform blood glucose change training functions and to generate or update the blood glucose change distribution record 1400 and the probability density correction record 1460 shown in FIGS. 25 and 26. This code may be executed during a training phase which may occur prior to and/or contemporaneously with forecasting as described with reference to the flowchart 200 shown in FIG. 3.

In various embodiments, the blood glucose change training code included in the block of codes 162 may direct the forecaster processor 100 to determine, for each time period in a day, a blood glucose change distribution record representing a density histogram spanning from −390 to 390 mg/dL per hour with steps of 30 mg/dL per hour.

For example, in some embodiments, the blood glucose change training code may direct the forecaster processor 100 to generate the blood glucose change distribution record 1400 shown in FIG. 25 to represent a density histogram based on blood glucose trend records stored in the location 148 of the storage memory 104 which have a 5th blood glucose value associated with a time between 12:00 pm and 1:00 pm.

The blood glucose change training code may direct the forecaster processor 100 to for each blood glucose trend record stored in the location 148 of the storage memory 104 and having a 5th blood glucose value associated with a time between 12:00 pm and 1:00 pm, determine the difference between the last blood glucose value and the 5th blood glucose value. The blood glucose change training code may direct the forecaster processor 100 to compute a density histogram of these differences such that the histogram spans from −390 to 390 by steps of 30 and to store a representation of the density histogram as the blood glucose change distribution record 1400. The blood glucose change training code may direct the forecaster processor 100 to prevent any probability density field from being set to 0 by fixing the minimum value of the probability density as 1/N where N is the total number of trend records having a 5th blood glucose value associated with a time between 12:00 pm and 1:00 pm.

The blood glucose change training code may direct the forecaster processor 100 to generate blood glucose change distribution records generally as described above, for each time period in a day.

In various embodiments, the blood glucose change training code may direct the forecaster processor 100 to generate the probability density correction record 1460 such that the probability density correction fields include values that represent a density histogram of blood glucose changes over time for all of the blood glucose trend records stored in the location 148 of the storage memory 104. Thus, the blood glucose change training code may direct the forecaster processor 100 to generate the probability density correction record 1460 generally similarly to as described above for the blood glucose change distribution record 1400, but considering all of the blood glucose trend records stored in the location 148 of the storage memory 104, regardless of the times associated with those trend records, such that the generated probability density correction record 1460 represents a density histogram that spans from −390 to 390 mg/dL per hour with steps of 30 mg/dL per hour.

In various embodiments, this may facilitate the development of condition centric libraries by adding penalties to trends/conditions that are over presented/and or under represented to create/simulate libraries for instance, libraries of running between 1-2 pm.

In some embodiments, the blood glucose change distribution record 1400 may represent a distribution p and the probability density correction record 1460 may represent a distribution p'. In the embodiment described above, the blood glucose change distribution record 1400 was calculated for one specific criterion (e.g. trends between 12-1 PM). In some embodiments, the forecaster processor 100 may be directed to handle multiple criteria by determining multiple probability distributions $p_1$, $p_2$ according to various models. For example, in some embodiments, respective distributions may be determined having regard to any or all of the following criteria: a time in the day, value of last point, slope of the trend and/or activity.

In some embodiments, if n criteria are being used, a weight may be calculated in the following manner:

$$w = \sqrt[n]{\frac{(p')^n}{\prod_{i=1}^{n} p_i}}$$

In some embodiments, n=4 criteria may be used. In some embodiments, the weight may be recalculated over-time.

In some embodiments, $$w = \sqrt[n]{\frac{(p')^n}{\prod_{i=1}^{n} p_i}}$$

and not the inverse may be used such that when p'>p it may be determined that an event or trend is overrepresented in the blood glucose trend records stored in the location 148 of the storage memory 104. Thus, the weight may be set to greater than one to increase the distance and reduce the chance of an over-represented trend being picked. In various embodiments, the weight may also increase the chance of an under-represented trend being picked.

Activity Information

Figure 27:
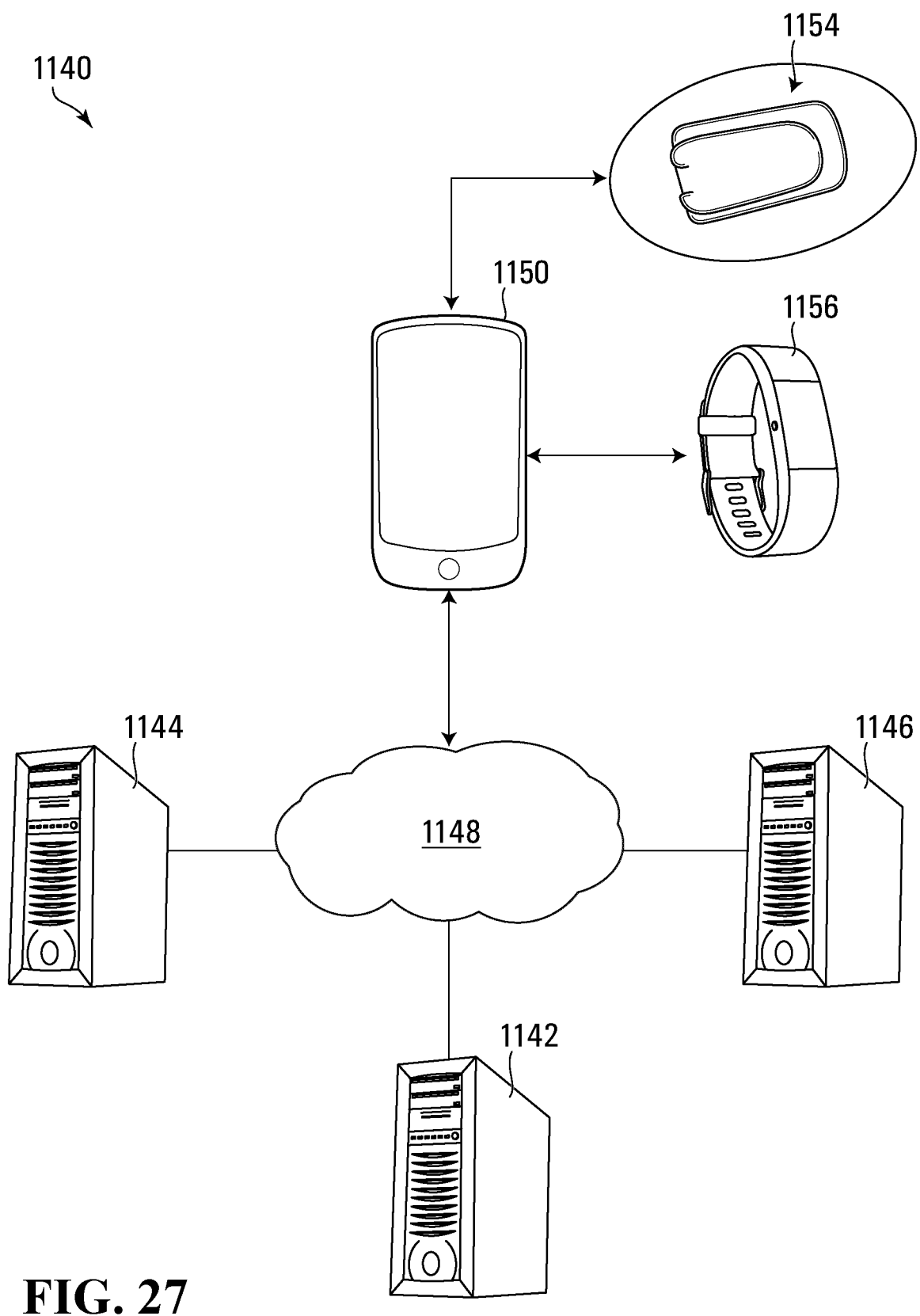
FIG. 27 is a schematic view of a system for facilitating physiological property forecasting for detecting disease complications in accordance with various embodiments of the invention.

Referring to FIG. 27, there is shown a system 1140 for physiological property forecasting in accordance with an embodiment. The system 1140 includes a forecaster 1142, a blood glucose data source 1144, a heart rate and activity level data source 1146, and a patient device 1150 in communication via a network 1148. The system 1140 also includes a blood glucose sensor 1154 and a heart rate and activity sensor 1156 in communication with the patient device 1150. In various embodiments, the heart rate and activity sensor 1156 may be implemented as an activity tracker, such as a Fitbit™ brand activity tracker, for example.

The system 1140 shown in FIG. 27 may function in generally similar ways to that of the system 10 shown in FIG. 1 and described above, but may use activity level information as contextual information in addition to or as an alternative to heart rate information, as described above. In various embodiments, the heart rate and activity sensor 1156 may be configured to sense and provide heart rate information as described above having regard to the heart rate sensor 26. The heart rate and activity sensor 1156 may also be configured to sense activity of the patient and to send activity information including activity values representing activity of the patient to the forecaster 1142 via the patient device 1150 and the heart rate and activity level data source 1146. The heart rate and activity level data source 1146 may act as an intermediary for providing the heart rate information and the activity information to the forecaster 1142.

Figure 28:
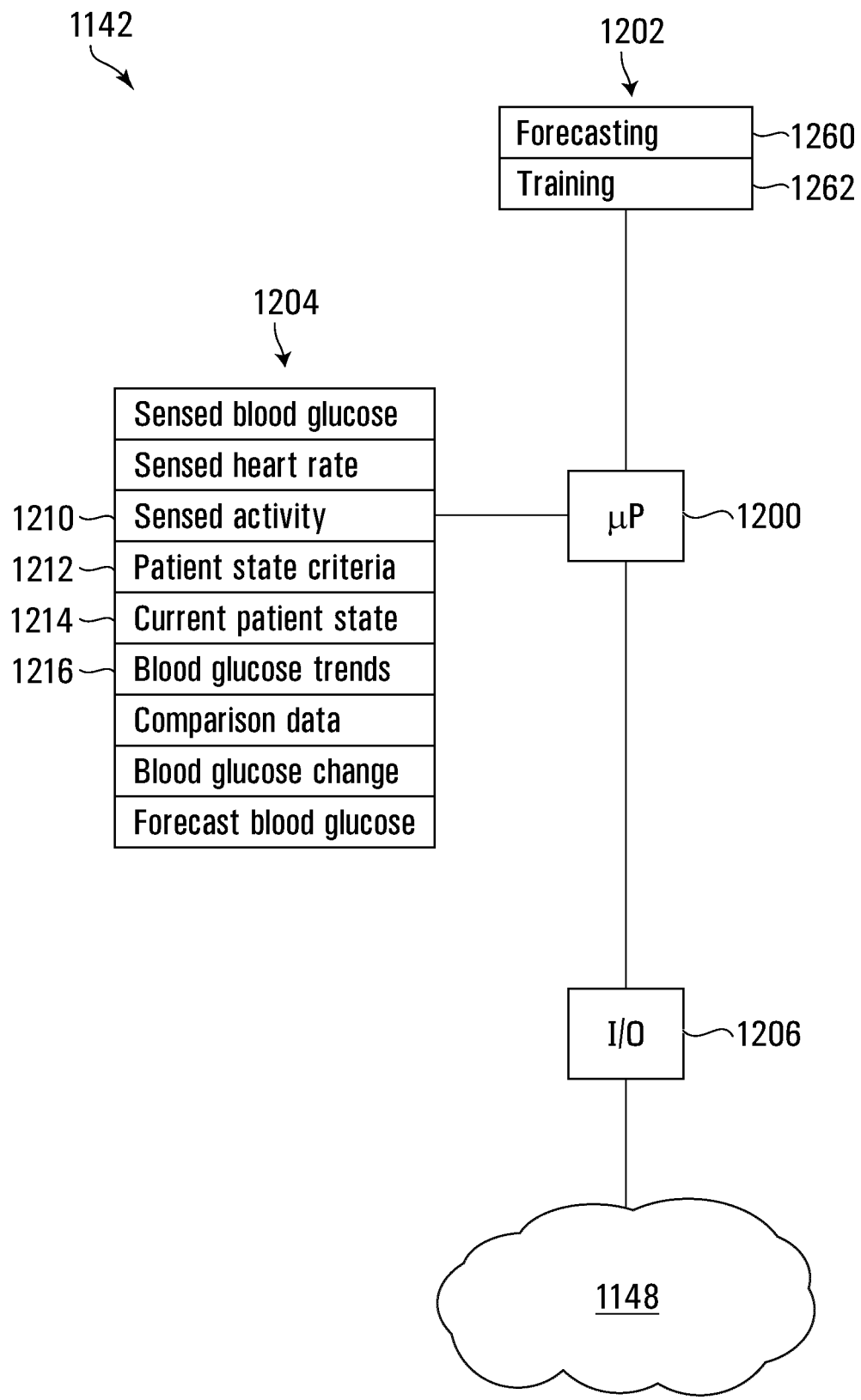
FIG. 28 is a schematic view of a forecaster shown in the system of FIG. 27 including a processor circuit in accordance with various embodiments of the invention.

Referring to FIG. 28, a schematic view of the forecaster 1142 of the system 1140 shown in FIG. 27 according to an embodiment is shown. The forecaster 1142 may be generally similar to the forecaster 12 shown in FIG. 2 but adapted to receive and use the activity information as contextual information. Referring to FIG. 26, the forecaster 1142 includes a forecaster processor 1200, a program memory 1202, a storage memory 1204, and an I/O interface 1206 in communication with the network 1148. The storage memory 1204 includes similar locations to those described above having regard to the storage memory 104 shown in FIG. 2 but also includes a location 1210 for storing sensed activity information. The program memory 1202 includes a block of codes 1260 for directing the forecaster 12 to perform forecasting functions and a block of codes 1262 for directing the forecaster processor 100 to perform training functions.

Figure 29:
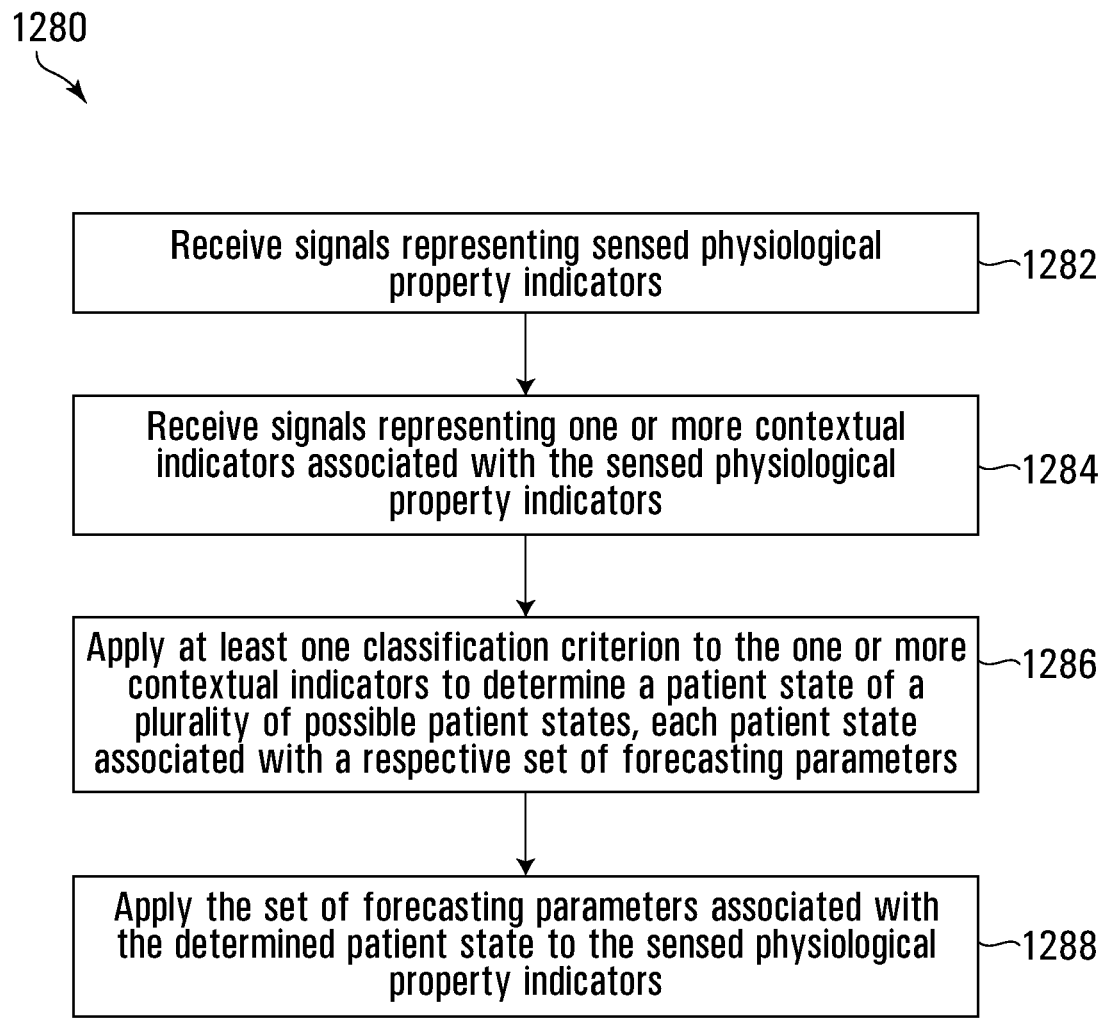
FIG. 29 is a flowchart depicting blocks of code for directing the forecaster of the system of FIG. 27 to perform forecasting functions in accordance with various embodiments of the invention.

In various embodiments, blocks of code included in the block of codes 1260 of the program memory 1202 shown in FIG. 26 may include blocks generally similar to the blocks shown in FIG. 3 included in the flowchart 200. Referring to FIG. 29 there is provided a flowchart 1280 depicting blocks of code that may be included in the block of codes 1260 of the program memory 1202 in accordance with various embodiments. The flowchart 1280 begins with block 1282 which directs the forecaster processor 1200 to receive signals representing sensed physiological property indicators. In various embodiments, block 1282 may be generally similar to block 202 of the flowchart 200 shown in FIG. 3 and described above.

Block 1284 of the flowchart 1280 shown in FIG. 29 then directs the forecaster processor 1200 shown in FIG. 26 to receive signals representing one or more contextual indicators associated with the sensed physiological property indicators. Block 1284 may include code generally similar to that included in block 204 of the flowchart 200 shown in FIG. 3 and may direct the forecaster processor 1200 to receive heart rate information and generate and store heart rate records as described above.

In various embodiments, block 1284 of the flowchart 1280 shown in FIG. 29 may direct the forecaster processor 1200 shown in FIG. 26 to also receive activity information from the heart rate and activity level data source 1146 shown in FIG. 27 and to generate and store activity records in the location 1210 of the storage memory 1204 representing the activity information. The activity information may include activity values representing activity levels of the patient, such as, for example, a distance walked or travelled by the patient, over a time period. In some embodiments, the activity values may represent a number of kilometers walked in one minute, for example.

An exemplary activity record is shown at 1300 in FIG. 30. The activity record 1300 includes an activity field 1302 and a time field 1304. The activity field 1302 stores an activity value representing a distance in kilometers travelled by the patient during a time period represented by a time value stored in the time field 1304. In various embodiments, block 1284 may direct the forecaster processor 1200 to generate and store a plurality of activity records generally similar to the activity record 1300 in the location 1210 of the storage memory 104.

Block 1286 of the flowchart 1280 shown in FIG. 29 then directs the forecaster processor 1200 to apply at least one classification to the one or more contextual indicators to determine a patient state of a plurality of possible patient states, each patient state associated with a respective set of forecasting parameters. In some embodiments, block 1286 may direct the forecaster processor 1200 to identify recent blood glucose levels and then to identify one or more heart rates associated with the identified blood glucose levels, generally as described above with reference to the flowchart 400 shown in FIG. 6. Block 1286 may then direct the forecaster processor 1200 to identify one or more activity levels associated with the identified blood glucose levels by identifying one or more activity records having time values that correspond to the time values associated with the identified blood glucose values.

Block 1286 of the flowchart 1280 shown in FIG. 29 may then direct the forecaster processor 1200 shown in FIG. 26 to determine whether the identified heart rate values and activity values are each within a respective range or 2D space. Block 1286 may direct the forecaster processor 1200 to determine whether an average of the identified heart rate values is within a heart rate value range and whether an average of the identified activity values is within an activity value range. For example, block 1286 may direct the forecaster processor 1200 to retrieve a patient state record 1340 as shown in FIG. 31 from the location 1212 of the storage memory 1204 to determine what ranges the heart rate values and activity values fall within.

Referring to FIG. 31, the patient state record 1340 includes a first state identifier field 1342 and associated heart rate lower and upper bound fields 1344 and 1346 and activity lower and upper bound fields 1348 and 1350. The patient state record 1340 also includes second, third, fourth, fifth, and sixth state identifier fields 1352, 1360, 1370, 1380, and 1390 and respective associated heart rate lower and upper bound fields and activity lower and upper bound fields.

In some embodiments, a state identifier field 1342 of "Awake and active (Sport)" may be associated with a heart rate range that indicates that the patient is awake and engaging in activity and an activity range that indicates that the patient is active. For example, in some embodiments, the state identifier of "Awake and active (Sport)" may be associated with heart rate lower and upper bounds of 112 bpm and 999 bpm and activity lower and upper bounds of 0.3 and 999 km. Thus, in some embodiments, the "Awake and active (Sport)" state, which is associated with doing sports or aerobic activity may only be detected once it is determined that both high heart rate and high activity data have been detected. This may facilitate more accurate determination of states.

In some embodiments, a state identifier field 1352 of "Elevated heart rate inactive" or "Stressed/Sickness may be associated with a heart rate range that indicates that the patient is awake and has an elevated heart rate and an activity range that indicates that the patient is not active. For example, in some embodiments, the state identifier of "Elevated heart rate inactive" may be associated with heart rate lower and upper bounds of about 112 bpm and 999 bpm and activity lower and upper bounds of about 0 and 0.3 km.

In some embodiments, a state identifier field 1360 of "Awake and inactive" may be associated with a heart rate range that indicates that the patient is awake but not engaging in activity and an activity range that indicates that the patient is not active. For example, in some embodiments, the state identifier of "Awake and inactive" may be associated with heart rate lower and upper bounds of 63 bpm and 112 bpm and activity lower and upper bounds of 0 and 0.3 km.

In some embodiments, a state identifier field 1370 of "Awake and active (low hr)" may be associated with a heart rate range that indicates that the patient is awake but not engaging in aerobic activity and an activity range that indicates that the patient is active. For example, in some embodiments, the state identifier of "Awake and inactive (low hr)" may be associated with heart rate lower and upper bounds of 63 bpm and 112 bpm and activity lower and upper bounds of 0.3 and 999 km.

In some embodiments, a state identifier field 1380 of "Asleep" or "Deep sleep (REM)" may be associated with a heart rate range that is low and indicates that the patient is asleep and an activity range that indicates that the patient is not active. For example, in some embodiments, the state identifier of "Deep sleep (REM)" may be associated with heart rate lower and upper bounds of about 0 bpm and 63 bpm and activity lower and upper bounds of about 0 and 0.01 km.

In some embodiments, a state identifier field 1390 of "Sleep (About to wake up)" may be associated with a heart rate range that and indicates that the patient is asleep and an activity range that indicates that the patient has engaged in some activity. For example, in some embodiments, the state identifier of "Sleep (About to wake up)" may be associated with heart rate lower and upper bounds of about 0 bpm and 63 bpm and activity lower and upper bounds of about 0.01 and 999 km.

Figure 32:
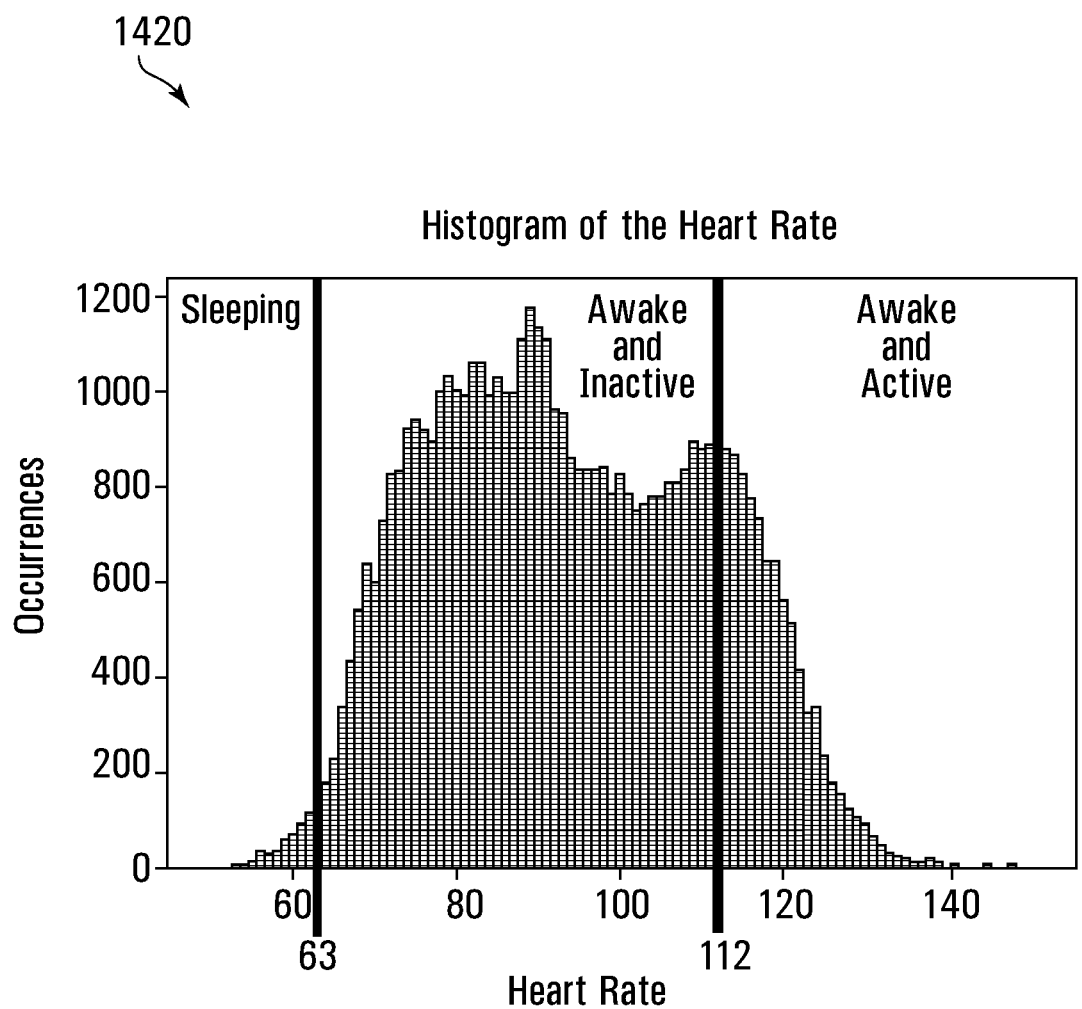
FIG. 32 is a representation of a histogram depicting exemplary heart rates represented by heart rate records stored by the forecaster of the system shown in FIG. 27, in accordance with various embodiments of the invention.

Referring to FIG. 32 there is shown a histogram 1420 depicting an exemplary distribution of heart rates for a patient, in accordance with one embodiment.

Block 1286 of the flowchart 1280 shown in FIG. 29 may direct the forecaster processor 1200 to compare the determined average heart rate value to the contents of the heart rate lower and upper bound fields of the patient state record 1340 shown in FIG. 31. Block 1286 may direct the forecaster processor 1200 to compare the determined average activity value to the contents of the activity lower and upper bound fields of the patient state record 1340 shown in FIG. 31. When it is determined which set of associated bounds the average heart rate value and average activity value falls within, block 1286 may direct the forecaster processor 1200 to determine a patient state as identified by the state identifier associated with the determined set of associated bounds.

In various embodiments, block 1286 of the flowchart 1280 shown in FIG. 29 may direct the forecaster processor 1200 shown in FIG. 28 to store the state identifier as a current patient state identifier in the location 1214 of the storage memory 104.

In various embodiments, generally as described above there may be stored in the location 1216 of the storage memory 1204 a plurality of glucose trend records, each associated with one of the state identifiers included in the patient state record 1340 shown in FIG. 31.

Referring to FIG. 29, block 1288 directs the forecaster processor 1200 to apply the set of forecasting parameters associated with the determined patient state to the sensed physiological property indicators to determine at least one forecast physiological property indicator representing a forecast physiological property of the patient at a future time. Block 1288 may include code generally similar to that of block 208 of the flowchart 200 shown in FIG. 3 and described above.

In various embodiments, the block of codes 1262 of the program memory 1202 shown in FIG. 28 may include code generally similar to that described above having regard to the block of codes 162 of the program memory 102 shown in FIG. 3. In some embodiments, the block of codes 1262 may include patient state training blocks of code for directing the forecaster processor 1200 to perform patient state training functions for generating or updating the patient state record 1340 shown in FIG. 31 and stored in the location 1214 of the storage memory 1204 shown in FIG. 28.

The patient state training blocks of code may direct the forecaster processor 1200 to identify clusters of sensed blood glucose values that are associated with similar heart rate values and activity values and to determine boundary heart rate values and activity values based on the identified clusters. The patient state training blocks of code may direct the forecaster processor 1200 to analyze a 2D space defined by heart rate values and activity values to determine the boundary heart rate values and activity values. The patient state training blocks of code may direct the forecaster processor 1200 to set state identifiers and corresponding heart rate lower and upper bound fields and activity lower and upper bound fields included in the patient state record 1340 based on the determined boundary heart rate values and activity values.

In some embodiments, additional or alternative states associated with respective heart rate ranges and activity ranges may be used and represented by the patient state record 1340 shown in FIG. 31. In some embodiments, heart rate information alone may be used to determine which of the following three states a patient may be in: "Asleep", "Awake and inactive", or "Awake and active" as per the histogram 1420 shown in FIG. 32.

Blood Oxygen Saturation

In some embodiments, a system generally similar to the system 1140 shown in FIG. 27 may be provided, which uses values representing blood oxygen saturation as contextual indicators. The system may include a blood oxygen saturation sensor for sensing blood oxygen saturation of the patient, and may function in generally similar ways to that of the system 1140 shown in FIG. 27 and described above.

In some embodiments, the system may store in storage memory a patient state record having a state identifier of "Awake and active", which may be associated with a heart rate range that indicates that the patient is awake and has an elevated heart rate, an activity range that indicates that the patient is active, and a blood oxygen saturation range that indicates that the patient has a low blood oxygen saturation level. For example, in some embodiments, the state identifier of "Awake and active" may be associated with heart rate lower and upper bounds of about 112 bpm and 999 bpm, activity lower and upper bounds of about 0.3 and 999 km, and blood oxygen saturation lower and upper bounds of about 97% and 99%.

In some embodiments, a state identifier of "Awake and inactive" may be associated with a heart rate range that indicates that the patient is awake but not engaging in activity, an activity range that indicates that the patient is not active, and a blood oxygen saturation range that indicates that the patient has high blood oxygen levels. For example, in some embodiments, the state identifier of "Awake and inactive" may be associated with heart rate lower and upper bounds of about 63 bpm and 112 bpm, activity lower and upper bounds of about 0 and 0.3 km, and blood oxygen saturation lower and upper bounds of about 99% and 100%.

In some embodiments, a state identifier of "Awake and elevated (Stressed/Sickness)" may be associated with a heart rate range that indicates that the patient is awake and has an elevated heart rate, an activity range that indicates that the patient is not active and a blood oxygen saturation range that indicates that the patient has high blood oxygen levels. For example, in some embodiments, the state identifier of "Awake and elevated (Stressed/Sickness)" may be associated with heart rate lower and upper bounds of about 112 bpm and 999 bpm, activity lower and upper bounds of about 0 and 0.3 km, and blood oxygen saturation lower and upper bounds of about 96% and 99%.

In some embodiments, a state identifier of "Awake and elevated (In Pain)" may be associated with a heart rate range that indicates that the patient is awake and has an elevated heart rate, an activity range that indicates that the patient is not active and a blood oxygen saturation range that indicates that the patient has low blood oxygen levels. For example, in some embodiments, the state identifier of "Awake and elevated (Stressed/Sickness)" may be associated with heart rate lower and upper bounds of about 112 bpm and 999 bpm, activity lower and upper bounds of about 0 and 0.3 km, and blood oxygen saturation lower and upper bounds of about 0% and 96%.

Various Embodiments

In some embodiments the system 10 shown in FIG. 1 or a system generally similar to the system 10 shown in FIG. 1 may be used to monitor and/or forecast various physiological properties, such as, for example, blood glucose levels, blood pressure, heart rate, electrocardiographic data, body temperature, blood oxygen saturation (e.g. $SpO_2$), respiratory data and/or breathing rate. The system may be configured to execute code generally similar to the code shown in the flowchart 200, using blood glucose levels, blood pressure, heart rate, electrocardiographic data, body temperature, blood oxygen saturation, respiratory data and/or breathing rate as the physiological properties, for example. In some embodiments, for example, by forecasting future blood glucose levels, blood pressure, heart rate, electrocardiographic data, body temperature, blood oxygen saturation, respiratory data and/or breathing rates, the system may facilitate a patient and/or clinician being able to prepare for or mitigate future hypoglycemia and hyperglycemia, cardiovascular problems, infection, arrhythmia, asthma, chronic obstructive pulmonary disease, and/or respiratory problems. For example, forecasting high blood pressure/heart rate, elevated body temperature and lower oxygen saturation may be used to detect infections. For example, elevated heart rate and low oxygen saturation may indicate an asthma attack.

In some embodiments, the blood glucose data source 14 and/or the heart rate data source 16 of the system 10 shown in FIG. 1 may be omitted and information may be sent directly from the patient device to the forecaster 12. In some embodiments, any or all of the patient device 20 and the sensors 24 and 26 may be implemented as a single combined device.

In the embodiment shown in FIG. 1, the forecaster 12 is separate from the patient device 20. This may facilitate the forecaster 12 being able to provide forecasting functionality for a plurality of patients and patient devices, which may be included in the system 10 in various embodiments. In various embodiments, separating the forecaster 12 and the patient device may also allow intensive computations to be done on a server which may be computationally more powerful than the patient device 20. However, in some embodiments, any or all of the functionality of the forecaster 12 may be implemented on the patient device 20. For example, in various embodiments, the patient device 20 may include any or all of the elements of the forecaster 12 shown in FIG. 3. In various embodiments, such an arrangement may reduce privacy concerns and/or avoid or reduce latency issues that arise from communication between the patient device 20 and the forecaster 12.

While various embodiments have been described above regarding a single patient for clarity and simplicity, in various embodiments, the forecaster 12 may be configured to perform forecasting and/or training for a plurality of patients. Accordingly, in various embodiments, the system 10 may include a plurality of patient devices and associated sensors, each generally similar to the patient device 20 and sensors 24 and 26 shown in FIG. 1. In such embodiments, each of the records described herein may be associated with a unique patient identifier.

In some embodiments, forecasting parameters other than the blood glucose trend records may be used. For example, in some embodiments the forecasting parameters may include a blood glucose change value representing an expected rate of change in blood glucose associated with a patient state. In such embodiments, a different blood glucose change value may be associated with each of the patient states and applying the forecasting parameters may involve forecasting future blood glucose values based on the blood glucose change value associated with a determined state. In various embodiments, other forecasting parameters may be used.

In some embodiments, block 524 of the flowchart 520 shown in FIG. 10 may direct the forecaster processor 100 shown in FIG. 2 to compare using a different or additional comparison process other than that described having regard to the flowchart 600. For example, in some embodiments, block 524 may direct the forecaster processor 100 to perform comparison using different comparison methods such as Polynomial approximation.

In some embodiments, block 524 may direct the forecaster processor 100 to perform comparison of derivatives. In some embodiments, block 524 may direct the forecaster processor 100 to perform polynomial approximation and comparison of coefficients.

In some embodiments, block 524 of the flowchart 520 shown in FIG. 10 may direct the forecaster processor 100 to calculate weights to be applied to determined differences using other or additional functions to those described above. For example, in some embodiments, block 524 may direct the forecaster processor 100 to perform retro-control wherein each trend record is associated with a weight. In various embodiments, all weights may start at 1 and if a trend record was used in prediction (i.e., selected at execution of block 526 of the flowchart 520 shown in FIG. 10) and the trend record represented was quite close to what was later observed in reality (e.g. relative error less than 15%), a block included in the block of codes 162 shown in FIG. 2, for example, may direct the forecaster processor 100 to increase the probability of selecting this trend record by decreasing the weight associated with the trend record. On the other hand, if the trend record was used in the prediction but it is quite far from the observed trend (e.g. average error more than 20%), the forecaster processor 100 may be directed to reduce the probability of the trend record being selected by increasing the weight associated with the trend record.

In some embodiments, block 604 may direct the forecaster processor 100 to determine the sum of differences by determining a modified Euclidean distance defined as:

$$d = 0.95 * \sqrt{\sum_{1}^{5} \left(\frac{i}{5}\right)[(a_i - a_5) - (b_i - b_5)]} + 0.05 * \sqrt{\sum_{i=1}^{5} \left(\frac{i}{5}\right)[a_i - b_i]}$$

The modified Euclidean distance may be treated generally as described above regarding the Euclidean distance.

In some embodiments, a comparison value may be determined for each of the trends using the following equation:

$$c_i = w_i * d_i * \text{offset}_i$$

Such that $c_i$ is the product of $w_i$ (the weight of the i-th trend being considered) and $d_i$ (the distance between the i-th trend of the library and the blood glucose values of the recently sensed blood glucose record 410 and an $\text{offset}_i$ parameter. In various embodiments, the $\text{offset}_i$ parameter may be used to artificially adjust the comparison value. In various embodiments, the $\text{offset}_i$ parameter may represent the difference between the most recently measured blood glucose value, m, and the $5^{th}$ point in the trend i of the library.

In some embodiments, as described above, the recently sensed blood glucose record 410 may store 5 blood glucose values. In various other embodiments, the recently sensed blood glucose record 410 may store fewer or additional blood glucose values spanning more or less time than as described above in connection with the recently sensed blood glucose record 410. In some embodiments, the recently sensed blood glucose record 410 may store blood glucose values spanning a time period of between about 20 minutes and about 30 minutes.

Similar changes and/or embodiments described herein having regard to the system 10 may also apply to the system 1140 shown in FIG. 27.

While specific embodiments of the invention have been described and illustrated, such embodiments should be considered illustrative of the invention only and not as limiting the invention as construed in accordance with the accompanying claims.

The invention claimed is:

1. A computer-implemented method of facilitating physiological property forecasting for detecting disease complications, the method comprising:
receiving signals representing sensed physiological property indicators, each of the sensed physiological property indicators representing a sensed physiological property of a patient at a respective time;
receiving signals representing one or more contextual indicators associated with the sensed physiological property indicators;
applying at least one classification criterion to the one or more contextual indicators to determine a patient state of a plurality of possible patient states, each patient state associated with a respective set of forecasting parameters; and
applying the set of forecasting parameters associated with the determined patient state to the sensed physiological property indicators to determine at least one forecast physiological property indicator representing a forecast physiological property of the patient at a future time;
wherein each of the sets of forecasting parameters includes a plurality of sets of historical physiological property indicators, each of the sets of historical physiological property indicators representing physiological properties of the patient during a respective historical time period, and wherein applying the set of forecasting parameters associated with the determined patient state comprises:
- comparing the sensed patient physiological property indicators to each of the sets of historical physiological property indicators included in the set of forecasting parameters associated with the determined patient state;
- selecting at least one of the sets of historical physiological property indicators included in the set of forecasting parameters associated with the determined patient state based on said comparing;
- generating a time-dependent function representing the selected at least one of the sets of historical physiological property indicators;
- determining the at least one forecast patient physiological property indicator using the generated time-dependent function;

wherein comparing the sensed patient physiological property indicators to each of the sets of historical physiological property indicators comprises, for each of the sets of historical physiological property indicators included in the set of forecasting parameters associated with the determined patient state, determining a sum of differences between the sensed patient physiological property indicators and respective ones of the historical physiological property indicators included in the set of historical physiological indicators;

wherein comparing the sensed patient physiological property indicators to each of the sets of historical physiological property indicators comprises, for each of the sets of historical patient physiological property indicators included in the set of forecasting parameters associated with the determined patient state, determining a weight associated with the set of historical physiological property indicators and applying the weight to the determined sum of differences;

wherein determining the weight associated with the set of historical physiological property indicators comprises:
- determining a change over time of at least some of the historical physiological property indicators included in the set;
- applying a probability density function to the change to determine a probability density for the change occurring within a time period associated with the sensed physiological property indicators; and
- determining the weight based on the determined probability density;

wherein each of the at least one forecast physiological property indicators includes a blood glucose value representing a forecast future blood glucose level of the patient; and wherein the method further comprises:
- adjusting, by a computer for managing insulin injection, an insulin injection to correct blood glucose levels in response to the forecast future blood glucose levels indicated by the at least one forecast physiological property indicator.

2. The method of claim 1 wherein the sensed physiological property indicators are sensed first physiological property indicators, each representing a sensed first physiological property of the patient, and wherein the one or more contextual indicators include sensed second physiological property indicators, each representing a second physiological property of the patient, said second physiological property being a different physiological property from the first physiological property.

3. The method of claim 1 wherein the one or more contextual indicators includes a heart rate value representing a heart rate of the patient and wherein applying the at least one classification criterion to the one or more contextual indicators comprises determining whether the heart rate value is within one of a plurality of heart rate value ranges.

4. The method of claim 1 wherein the one or more contextual indicators includes an activity value representing an activity level of the patient and wherein applying the at least one classification criterion to the one or more contextual indicators comprises determining whether the activity value is within one of a plurality of activity value ranges.

5. The method of claim 1 further comprising:
- receiving signals representing physiological property forecasting training information, the training information including:
  - the historical physiological property indicators included in the plurality of sets of historical physiological property indicators; and
  - contextual indicators, each associated with at least one of the historical physiological property indicators;
- identifying the plurality of sets of historical physiological property indicators from the historical physiological property indicators;
- classifying each of the sets of historical physiological property indicators based on the contextual indicators associated with the physiological indicators included in the sets, said classifying comprising, for each of the sets of historical physiological property indicators:
- applying at least one classification criterion to one or more of the contextual indicators associated with the set of historical physiological property indicators; and
- associating the set of historical physiological property indicators with one of the plurality of possible patient states.

6. A system for facilitating physiological property forecasting for detecting disease complications, the system comprising a forecaster device having at least one processor configured to:
- receive signals representing sensed physiological property indicators, each of the sensed physiological property indicators representing a sensed physiological property of a patient at a respective time;
- receive signals representing one or more contextual indicators associated with the sensed physiological property indicators;
- apply at least one classification criterion to the one or more contextual indicators to determine a patient state of a plurality of possible patient states, each patient state associated with a respective set of forecasting parameters; and
- apply the set of forecasting parameters associated with the determined patient state to the sensed physiological property indicators to determine at least one forecast physiological property indicator representing a forecast physiological property of the patient at a future time;
- wherein each of the sets of forecasting parameters includes a plurality of sets of historical physiological property indicators, each of the sets of historical physiological property indicators representing physiological properties of the patient during a respective historical time period, and wherein applying the set of forecasting parameters associated with the determined patient state comprises:
  - comparing the sensed patient physiological property indicators to each of the sets of historical physiological property indicators included in the set of forecasting parameters associated with the determined patient state;

selecting at least one of the sets of historical physiological property indicators included in the set of forecasting parameters associated with the determined patient state based on said comparing;

generating a time-dependent function representing the selected at least one of the sets of historical physiological property indicators; and determining the at least one forecast patient physiological property indicator using the generated time-dependent function;

wherein comparing the sensed patient physiological property indicators to each of the sets of historical physiological property indicators comprises, for each of the sets of historical physiological property indicators included in the set of forecasting parameters associated with the determined patient state, determining a sum of differences between the sensed patient physiological property indicators and respective ones of the historical physiological property indicators included in the set of historical physiological indicators;

wherein comparing the sensed patient physiological property indicators to each of the sets of historical physiological property indicators comprises, for each of the sets of historical patient physiological property indicators included in the set of forecasting parameters associated with the determined patient state, determining a weight associated with the set of historical physiological property indicators and applying the weight to the determined sum of differences;

wherein determining the weight associated with the set of historical physiological property indicators comprises:
  determining a change over time of at least some of the historical physiological property indicators included in the set;
  applying a probability density function to the change to determine a probability density for the change occurring within a time period associated with the sensed physiological property indicators; and
  determining the weight based on the determined probability density;

wherein each of the at least one forecast physiological property indicators includes a blood glucose value representing a forecast future blood glucose level of the patient;

wherein the system further comprises a computer for managing insulin injection; and wherein the computer for managing insulin injection is configured to:
  receive the at least one forecast physiological property indicators; and
  adjust an insulin injection to correct blood glucose levels in response to the forecast future blood glucose levels indicated by the at least one forecast physiological property indicators.

7. The system of claim 6, further comprising:
a blood glucose sensor;
a patient device; and
a server computing device separate from the patient device and the blood glucose sensor;
wherein the server computing device includes the forecaster device; and
wherein the patient device is configured to transmit the signals representing the sensed physiological property indicators to the server computing device.

8. The system of claim 6, further comprising:
a blood glucose sensor; and
a patient device;
wherein the patient device is configured to receive the signals representing the sensed physiological property indicators from the blood glucose sensor; and
wherein the patient device includes the forecaster device.

9. A non-transitory computer readable medium having stored thereon codes which when executed by at least one processor cause the at least one processor to:
  receive signals representing sensed physiological property indicators, each of the sensed physiological property indicators representing a sensed physiological property of a patient at a respective time;
  receive signals representing one or more contextual indicators associated with the sensed physiological property indicators;
  apply at least one classification criterion to the one or more contextual indicators to determine a patient state of a plurality of possible patient states, each patient state associated with a respective set of forecasting parameters; and
  apply the set of forecasting parameters associated with the determined patient state to the sensed physiological property indicators to determine at least one forecast physiological property indicator representing a forecast physiological property of the patient at a future time;
  wherein each of the sets of forecasting parameters includes a plurality of sets of historical physiological property indicators, each of the sets of historical physiological property indicators representing physiological properties of the patient during a respective historical time period, and wherein applying the set of forecasting parameters associated with the determined patient state comprises:
    comparing the sensed patient physiological property indicators to each of the sets of historical physiological property indicators included in the set of forecasting parameters associated with the determined patient state;
    selecting at least one of the sets of historical physiological property indicators included in the set of forecasting parameters associated with the determined patient state based on said comparing;
    generating a time-dependent function representing the selected at least one of the sets of historical physiological property indicators; and
    determining the at least one forecast patient physiological property indicator using the generated time-dependent function;
  wherein comparing the sensed patient physiological property indicators to each of the sets of historical physiological property indicators comprises, for each of the sets of historical physiological property indicators included in the set of forecasting parameters associated with the determined patient state, determining a sum of differences between the sensed patient physiological property indicators and respective ones of the historical physiological property indicators included in the set of historical physiological indicators;
  wherein comparing the sensed patient physiological property indicators to each of the sets of historical physiological property indicators comprises, for each of the sets of historical patient physiological property indicators included in the set of forecasting parameters associated with the determined patient state, determining a weight associated with the set of historical physiological property indicators and applying the weight to the determined sum of differences;
wherein determining the weight associated with the set of historical physiological property indicators comprises:
determining a change over time of at least some of the historical physiological property indicators included in the set;
applying a probability density function to the change to determine a probability density for the change occurring within a time period associated with the sensed physiological property indicators; and
determining the weight based on the determined probability density;
wherein each of the at least one forecast physiological property indicators includes a blood glucose value representing a forecast future blood glucose level of the patient; and
wherein the codes further cause the at least one processor to:
cause a computer for managing insulin injection to adjust an insulin injection to correct blood glucose levels in response to the forecast future blood glucose levels indicated by the at least one forecast physiological property indicator.

10. A system for facilitating physiological property forecasting for detecting disease complications, the system comprising:
means for receiving signals representing sensed physiological property indicators, each of the sensed physiological property indicators representing a sensed physiological property of a patient at a respective time;
means for receiving signals representing one or more contextual indicators associated with the sensed physiological property indicators;
means for applying at least one classification criterion to the one or more contextual indicators to determine a patient state of a plurality of possible patient states, each patient state associated with a respective set of forecasting parameters; and
means for applying the set of forecasting parameters associated with the determined patient state to the sensed physiological property indicators to determine at least one forecast physiological property indicator representing a forecast physiological property of the patient at a future time;
wherein each of the sets of forecasting parameters includes a plurality of sets of historical physiological property indicators, each of the sets of historical physiological property indicators representing physiological properties of the patient during a respective historical time period, and wherein applying the set of forecasting parameters associated with the determined patient state comprises means for:
comparing the sensed patient physiological property indicators to each of the sets of historical physiological property indicators included in the set of forecasting parameters associated with the determined patient state;
selecting at least one of the sets of historical physiological property indicators included in the set of forecasting parameters associated with the determined patient state based on said comparing;
generating a time-dependent function representing the selected at least one of the sets of historical physiological property indicators; and
determining the at least one forecast patient physiological property indicator using the generated time-dependent function;
wherein comparing the sensed patient physiological property indicators to each of the sets of historical physiological property indicators comprises, for each of the sets of historical physiological property indicators included in the set of forecasting parameters associated with the determined patient state, determining a sum of differences between the sensed patient physiological property indicators and respective ones of the historical physiological property indicators included in the set of historical physiological indicators;
wherein comparing the sensed patient physiological property indicators to each of the sets of historical physiological property indicators comprises, for each of the sets of historical patient physiological property indicators included in the set of forecasting parameters associated with the determined patient state, determining a weight associated with the set of historical physiological property indicators and applying the weight to the determined sum of differences;
wherein determining the weight associated with the set of historical physiological property indicators comprises:
determining a change over time of at least some of the historical physiological property indicators included in the set;
applying a probability density function to the change to determine a probability density for the change occurring within a time period associated with the sensed physiological property indicators; and
determining the weight based on the determined probability density;
wherein each of the at least one forecast physiological property indicators includes a blood glucose value representing a forecast future blood glucose level of the patient;
wherein the system further comprises means for managing insulin injection; and
wherein the means for managing insulin injection includes:
means for receiving the at least one forecast physiological property indicators; and
means for adjusting an insulin injection to correct blood glucose levels in response to the forecast future blood glucose levels indicated by the at least one forecast physiological property indicators.

* * * * *